United States Patent [19]

Göschke et al.

[11] Patent Number: 5,606,078
[45] Date of Patent: Feb. 25, 1997

[54] 3,5-DISUBSTITUTED TETRAHYDROFURAN-2-ONES

[75] Inventors: Richard Göschke, Bottmingen; Peter Herold, Arlesheim, both of Switzerland; Pascal Rigollier, Sierentz, France; Jürgen K. Maibaum, Weil-Haltingen, Germany

[73] Assignee: Ciba-Geigy Corporation, Tarrytown, N.Y.

[21] Appl. No.: 416,237

[22] Filed: Apr. 4, 1995

[30] Foreign Application Priority Data

Apr. 18, 1994 [CH] Switzerland ............................ 1169/94
Jan. 30, 1995 [CH] Switzerland ............................ 246/95

[51] Int. Cl.⁶ ............................................ C07D 307/33
[52] U.S. Cl. .............................. 549/321; 549/323
[58] Field of Search ............................ 549/321, 323

[56] References Cited

U.S. PATENT DOCUMENTS

| | | | |
|---|---|---|---|
| 4,613,676 | 9/1986 | Fuhrer et al. | 560/39 |
| 4,898,877 | 2/1990 | Meyer et al. | 514/521 |
| 5,091,425 | 2/1992 | Bradbury et al. | 514/228.5 |
| 5,254,697 | 10/1993 | Waterson | 549/313 |

FOREIGN PATENT DOCUMENTS

| | | |
|---|---|---|
| 0414342 | 2/1991 | European Pat. Off. |
| 6-3063673 | 9/1986 | Japan. |
| 9000166 | 1/1990 | WIPO. |

OTHER PUBLICATIONS

Fray A. et al, The Journal of Organic Chemistry 51(25):4828–4833 (1986).
Wuts, P. et al, The Journal of Organic Chemistry 57(25): 6696–6700 (1992).
Prasad J. et al, Tetrahedron Letters 31(13):1803–1806 (1992).
Meints M. et al. Liebigs, Ann. Chem. 93(5): 527–530 (1993), (English Translation).
Hormuth, S. et al. Angew. Chem. Tot. Ed. 32(10): 1513–1514 (1993), (English Translation).
Bradbury et al. "An Efficient Synthesis Of The γ-Lactone Corresponding To A Hydroxyethylene Dipetide Isotere Using Stereoselective Bromolactonisation Of A Chiral Acyloxazolidinone" Tetrahedron Letters, 30(29): 3845–3848 (1989).
Bradbury et al. "1,2,4–Triazole [4,3–a] pyrazine Derivatives with Human Renin Inhibitory Activity , 2.¹ Synthesis, Biological Properties and Molecular Modeling of Hydroxyethylene Isostere Derivatives" J. Med. Chem, 33: 2335–2342 (1990).

*Primary Examiner*—Ba K. Trinh
*Attorney, Agent, or Firm*—Gregory D. Ferraro

[57] ABSTRACT

Compounds of formula I

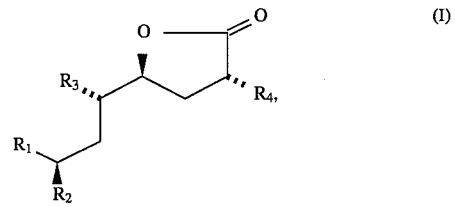

wherein
$R_1$ is free or esterified carboxy, hydroxymethyl or formyl,
$R_2$ and $R_4$ are each independently of the other aliphatic, cycloaliphatic-aliphatic, araliphatic or heteroarylaliphatic radicals and
$R_3$ is azido, or amino that is aliphatically or aralipnatically substituted and/or protected by an amino-protecting group, and the salts thereof, are valuable intermediates in the preparation of medicinal active ingredients, for example of compounds of formula II

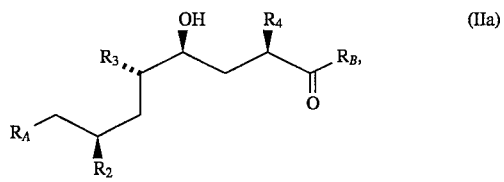

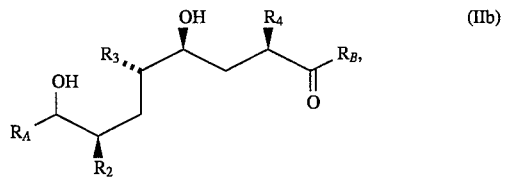

wherein
$R_A$ is an aromatic or heteroaromatic radical,
$R_2$ and $R_4$ are each independently of the other aliphatic, cycloaliphatic, cycloaliphaticaliphatic or araliphatic radicals,
$R_3$ is unsubstituted or N-mono- or N,N-di-lower alkylated or N-lower alkanoylated amino, and
$R_B$ is an aliphatically, cycloaliphatically or heteroaromatically-aliphatically substituted amino group, and the salts thereof, which can be used, for example, as antihypertensives.

7 Claims, No Drawings

3,5-DISUBSTITUTED TETRAHYDROFURAN-2-ONES

The invention relates to compounds of formula I

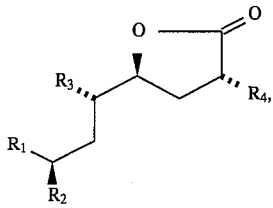

wherein $R_1$ is free or esterified carboxy, hydroxymethyl or formyl, $R_2$ and $R_4$ are each independently of the other aliphatic, cycloaliphatic-aliphatic, araliphatic or heteroarylaliphatic radicals, and $R_3$ is azido, or amino that is aliphatically or araliphatically substituted and/or protected by an amino-protecting group, and to the salts thereof, to processes for the preparation thereof and to the use thereof as intermediates in the preparation of medicinal active ingredients.

Free or esterified carboxy is, for example, carboxy, lower alkoxycarbonyl or unsubstituted or lower alkyl-, lower alkoxy-, halo- and/or trifluoromethyl-substituted phenyl-lower alkoxy-carbonyl.

Aliphatic radicals are, for example, lower alkyl radicals, lower alkenyl, lower alkoxy or lower alkylthio, preferably methyl or branched $C_1$–$C_4$ alkyl, such as isopropyl.

Cycloaliphatic-aliphatic radicals are, for example, 3- to 7-membered, especially 3- to 5-membered, cycloalkyl-lower alkyl radicals.

Araliphatic radicals are, for example, aryl-lower alkyl, such as phenyl-lower alkyl or naphthyl-lower alkyl, that is unsubstituted or mono-, di- or tri-substituted by lower alkyl, lower alkoxy, hydroxy, lower alkylamino, di-lower alkylamino, halogen and/or by trifluoromethyl.

Heteroarylaliphatic radicals contain as heteroaryl radical, for example, an optionally benzofused 5- or 6-membered mono- or di-azaaryl radical or 5-membered oxa- or thia-aryl radical and are, for example, unsubstituted or lower alkyl-, lower alkoxy-, hydroxy-, halo-, nitro-and/or amino-substituted pyridyl-lower alkyl, indolyl-lower alkyl, quinolinyl-lower alkyl, pyrimidinyl-lower alkyl, furyl-lower alkyl, benzofuranyl-lower alkyl or thienyl-lower alkyl.

Unsubstituted or aliphatically or araliphatically substituted amino is, for example, unsubstituted or aliphatically mono- or di-substituted, araliphatically mono-substituted or araliphatically and aliphatically di-substituted amino, such as lower alkylamino, di-lower alkylamino, lower alkanoylamino or N-lower alkanoyl-N-lower alkylamino, or unsubstituted or lower alkyl-, lower alkoxy-, hydroxy-, halo-, nitro- and/or amino-substituted phenyl-lower alkylamino, N-lower alkyl-N-phenyl-lower alkylamino or N-lower alkanoyl-N-phenyl-lower alkylamino.

Aliphatically or araliphatically substituted amino protected by an amino-protecting group is, for example, amino, lower alkylamino, lower alkanoylamino or unsubstituted or lower alkyl-, lower alkoxy-, hydroxy-, halo-, nitro- and/or amino-substituted phenyl-lower alkylamino, N-lower alkyl-N-phenyl-lower alkylamino or N-lower alkanoyl-N-phenyl-lower alkylamino protected by an acyl group derived from a semi-ester of carbonic acid or of an aromatic carboxylic acid and/or by silyl. Acyl groups derived from a semi-ester of carbonic acid are, for example, lower alkoxycarbonyl or unsubstituted or lower alkyl-, lower alkoxy-, halo- and/or trifluoromethyl-substituted phenyl-lower alkoxycarbonyl, and silyl is especially tri-lower alkylsilyl, e.g. trimethylsilyl.

Unsubstituted or aliphatically or araliphatically substituted amino protected by an acyl group derived from a semi-ester of carbonic acid or by silyl is accordingly, for example, N-lower alkoxycarbonylamino, N-lower alkyl-N-lower alkoxycarbonyl-amino, N-lower alkanoyl-N-lower alkoxycarbonyl-amino, N-lower alkoxycarbonyl-N-phenyl-lower alkylamino, N-phenyl-lower alkoxycarbonylamino, N-lower alkyl-N-phenyl-lower alkoxycarbonylamino, N-lower alkanoyl-N-phenyl-lower alkoxycarbonyl-amino, N-phenyl-lower alkoxycarbonyl-N-phenyl-lower alkylamino, N-tri-lower alkylsilylamino, N-lower alkyl-N-tri-lower alkylsilylamino, N-lower alkanoyl-N-tri-lower alkylsilylamino or N-tri-lower alkylsilyl-N-phenyl-lower alkylamino.

Hereinbefore and hereinafter, lower radicals and compounds are to be undersood as being, for example, those having up to and including 7, preferably up to and including 4, carbon atoms.

Benzofuranyl-lower alkyl is, for example, benzofuranyl-$C_1$–$C_4$ alkyl, such as benzofuranyl-methyl, 1-benzofuranyl-ethyl, 2-benzofuranylethyl, 3-benzofuranylpropyl or 4-benzofuranyl-butyl.

Quinolinyl-lower alkyl is, for example, quinolinyl-$C_1$–$C_4$ alkyl, such as quinolinylmethyl, 1-quinolinylethyl, 2-quinolinylethyl, 3-quinolinylpropyl or 4-quinolinylbutyl.

Cycloalkyl-lower alkyl is, for example, cyclopropyl-, cyclobutyl-, cyclopentyl- or cyclohexyl-$C_1$–$C_4$ alkyl, such as cyclopropyl-, cyclobutyl-, cyclopentyl- or cyclohexyl-methyl, 1-cyclopropyl-, 1-cyclobutyl-, 1-cyclopentyl- or 1-cyclohexyl-ethyl, 2-cyclopropyl-, 2-cyclobutyl-, 2-cyclopentyl- or 2-cyclohexyl-ethyl, 3-cyclopropyl-, 3-cyclobutyl-, 3-cyclopentyl- or 3-cyclohexyl-propyl or 4-cyclopropyl-, 4-cyclobutyl-, 4-cyclopentyl- or 4-cyclohexyl-butyl.

Di-lower alkylamino is, for example, di-$C_1$–$C_4$ alkylamino, such as dimethylamino, N-methyl-N-ethylamino, diethylamino, N-methyl-N-propylamino or N-butyl-N-methylamino.

Furyl-lower alkyl is, for example, furyl-$C_1$–$C_4$ alkyl, such as furyl-methyl, 1-furylethyl, 2-furylethyl, 3-furylpropyl or 4-furylbutyl.

Halogen is, for example, halogen having an atomic number of up to and including 35, such as chlorine or bromine, also fluorine.

Indolyl-lower alkyl is, for example, indolyl-$C_1$–$C_4$ alkyl, such as indolylmethyl, 1-indolylethyl, 2-indolylethyl, 3-indolylpropyl or 4-indolylbutyl.

N-Lower alkyl-N-phenyl-lower alkoxycarbonyl-amino is, for example, N-$C_1$–$C_4$alkyl-$C_1$–$C_7$-alkanoyl-amino, such as N-methyl-, N-ethyl-, N-propyl-, N-isopropyl-, N-butyl- or N-tert-butyl-N-acetyl-amino or N-methyl-, N-ethyl-, N-propyl-, N-isopropyl-, N-butyl- or N-tert-butyl-N-pivaloyl-amino.

N-Lower alkanoyl-N-lower alkoxycarbonyl-amino is, for example, N-$C_1$-$C_7$alkanoyl-$C_1$–$C_4$-alkoxycarbonyl-amino, such as N-acetyl-N-tert-butyloxycarbonyl-amino.

N-Lower alkanoyl-N-lower alkyl-amino is, for example, N-$C_1$–$C_7$alkanoyl-N-$C_{1-C4}$alkyl-amino, such as N-acetyl-N-methyl-amino, N-acetyl-N-ethyl-amino, N-acetyl-N-propyl-amino, N-acetyl-N-butyl-amino, N-pivaloyl-N-methyl-amino, N-pivaloyl-N-ethyl-amino, N-pivaloyl-N-propyl-amino or N-pivaloyl-N-butyl-amino.

N-Lower alkanoyl-N-phenyl-lower alkoxycarbonyl-amino is, for example, N-$C_1$–$C_7$alkanoyl-N-$C_1$–$C_4$alkanoyl- N-$C_1$–$C_4$phenylalkoxycarbonyl-amino, such as N-acetyl-N-benzyloxycarbonyl-amino.

N-Lower alkanoyl-N-phenyl-lower alkyl-amino is, for example, N-$C_1$–$C_7$alkanoyl-N-$C_1$–$C_4$-phenylyl-amino, such as N-acetyl-N-benzylamino or N-acetyl-N-(2-phenylethyl)-amino.

N-Lower alkanoyl-N-tri-lower alkylsilyl-amino is, for example, N-$C_1$–$C_7$alkanoyl-N-$C_1$–$C_4$-tri- $C_1$–$C_4$alkylsilyl-amino, such as N-acetyl-N-trimethylsilyl-amino.

N-Lower alkoxycarbonyl-N-phenyl-lower alkylamino is, for example, N-$C_1$–$C_4$alkoxycarbonyl-N-phenyl-$C_1$–$C_4$-alkyl-amino, such as N-tert-butyloxycarbonyl-N-benzyl-amino.

Lower alkoxy is, for example, $C_1$–$C_7$alkoxy, preferably $C_1$–$C_5$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkoxycarbonylamino is, for example, $C_1$–$C_7$alkoxycarbonylamino, preferably $C_1$–$C_5$- alkoxycarbonylamino, such as methoxycarbonylamino, ethoxycarbonylamino, propyloxycarbonylamino, isopropyloxycarbonylamino, butyloxycarbonylamino, isobutyloxycarbonyl-amino, sec-butyloxycarbonylamino, tert-butyloxyamino, pentyloxycarbonyl-amino or a hexyloxy-carbonylamino or heptyloxycarbonylamino group.

N-Lower alkyl-N-lower alkoxycarbonyl-amino is, for example, N-$C_1$–$C_4$alkyl-N-$C_1$–$C_4$alkoxy-carbonyl-amino, such as N-methyl-, N-ethyl-, N-propyl-, N-isopropyl-, N-butyl- or N-tert-butyl-N-tert-butyloxcarbonyl-amino.

N-Lower alkyl-N-phenyl-lower alkyl-amino is, for example, N-$C_1$–$C_4$alkyl-N-phenyl-$C_1$–$C_4$alkyl-amino, such as N-methyl-, N-ethyl-, N-propyl-, N-isopropyl-, N-butyl- or N-tert-butyl-N-benzl-amino.

N-Lower alkyl-N-tri-lower alkylsilyl-amino is, for example, N-$C_1$–$C_4$alkyl-N-tri-$C_1$–$C_4$alkylsilyl-amino, such as N-methyl-, N-ethyl-, N-propylo, N-isopropyl-, N-butyl- or N-tert-butyl-N-tri-methylsilyl-amino.

N-Phenyl-lower alkoxycarbonyl-N-phenyl-lower alkylamino is, for example, N-phenyl-$C_1$–$C_4$-alkoxycarbonyl-N-phenyl- $C_1$–$C_4$alkyl-amino, such as N-benzyl-N-benzyloxycarbonyl-amino.

N-Phenyl-lower alkoxycarbonylamino is, for example, N-phenyl-$C_1$–$C_4$alkoxycarbonylamino, such as N-benzyloxycarbonylamino.

N-Tri-lower alkylsilyl-N-phenyl-lower alkylamino is, for example, N-tri-$C_1$–$C_4$alkyl-N-phenyl-$C_1$–$C_4$alkyl- amino, such as N-benzyl-N-trimethylsilyl-amino.

N-Tri-lower alkylsilylamino is, for example, N-tri-$C_1$–$C_4$alkylamino, such as N-trimethylsilyl-amino.

Naphthyl-lower alkyl radicals are, for example, naphthyl-$C_1$–$C_4$alkyl radicals, such as 1- or 2-naphthylmethyl, 2-(1- or 2-naphthyl)ethyl, 3-(1- or 2-naphthyl)propyl or 4-(1- or 2-naphthyl)-butyl.

Lower alkanoylamino is, for example, N-$C_1$–$C_7$alkanoylamino, such as acetylamino or pivaloylamino.

Lower alkenyl is, for example, $C_1$–$C_7$alkenyl, such as vinyl or allyl.

Lower alkoxy is, for example, $C_1$–$C_7$alkoxy, preferably $C_1$–$C_5$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkyl may be straight-chained or branched and/or bridged and is, for example, corresponding $C_1$–$C_7$alkyl, such as methyl, ethyl, propyl, isopropyl, butyl, isobutyl, sec-butyl, tert-butyl, or a pentyl, hexyl or heptyl group. Lower alkyl $R_2$ or $R_3$ is especially $C_2$–$C_7$alkyl, lower alkyl $R_5$ or $R_7$ is especially branched $C_3$–$C_7$alkyl and lower alkyl $R_8$ or $R_3$ is, for example, straight-chained, branched or bridged $C_3$–$C_7$alkyl.

Lower alkylamino is, for example, $C_1$–$C_4$alkylamino, such as methylamino, ethylamino, propylamino, butylamino, isobutylamino, sec-butylamino or tert-butylamino.

Lower alkylthio is, for example, $C_1$–$C_4$alkylthio, such as methylthio, ethylthio, propylthio, butylthio, isobutylthio, sec-butylthio or tert-butylthio.

Phenyl-lower alkylamino is, for example, phenyl-$C_1$–$C_4$alkylamino, such as benzylamino, 1 - or 2-phenethylamino, 3-phenylpropylamino or 4-phenylbutylamino.

Phenyl-lower alkyl is, for example, phenyl-$C_1$–$C_4$alkyl, such as benzyl, 1 - or 2-phenethyl, 3-phenylpropyl or 4-phenylbutyl.

Pyridyl-lower alkyl is, for example, pyridinyl-$C_1$–$C_4$alkyl, such as pyridinylmethyl, 1- or 2-pyridinylethyl, 3-pyridinylpropyl or 4-pyddinylbutyl.

Pyrimidinyl-lower alkyl is, for example, pyrimidinyl-$C_1$–$C_4$alkyl, such as pyrimidinylmethyl, 1- or 2-pyrimidinylethyl, 3-pyrimidinylpropyl or 4-pyrimidinylbutyl.

Thienyl-lower alkyl is, for example, thienyl-$C_1$–$C_4$alkyl, such as thienylmethyl, 1- or 2-thienyl-ethyl, 3-thienylpropyl or 4-thienylbutyl.

Salts of compounds having salt-forming groups are especially acid addition salts, salts with bases or, where several salt-forming groups are present, can also be mixed salts or internal salts.

Such salts are formed, for example, by compounds of formula I having an acid group, for example a carboxy group, and are, for example, salts thereof with suitable bases, such as non-toxic metal salts derived from metals of groups Ia, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkyl-amines, or with quaternary ammonium bases, for example with methyl-, ethyl-, diethyl- or triethyl-amine, mono-, bis- or tris-(2-hydroxy-lower alkyl)amines, such as ethanol-, diethanol-or triethanol-amine, tris(hydroxymethyl)methylamine or 2-hydroxy-tert-butylamine, N,N-di-lower alkyl-N-(hydroxy-lower alkyl)-amine, such as N,N-dimethyl-N-(2-hydroxyethyl)-amine, or N-methyl-D-glucamine, or quaternary ammonium hydroxides, such as tetrabutyl-ammonium hydroxide.

The compounds of formula I having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, such as the α-amino acids mentioned hereinbefore, and with methanesulfonic acid, ethanesulfonic acid, 2-hydroxyethanesulfonic acid, ethane-1,2-disulfonic acid, benzenesulfonic acid, 4-methyl-benzenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

For isolation and purification purposes it is also possible to use pharmaceutically unacceptable salts.

The compounds of formula I are valuable intermediates in the preparation of medicinal active ingredients, for example of compounds of formulae IIa and IIb

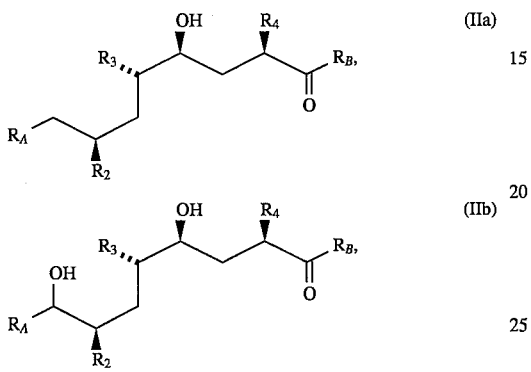

wherein $R_A$ is an aromatic or heteroaromatic radical, $R_2$ and $R_4$ are each independently of the other aliphatic, cycloaliphatic, cycloaliphatic-aliphatic or araliphatic radicals, $R_3$ is unsubstituted or N-mono- or N, N-di-lower alkylated or N-lower alkanoylated amino, and $R_B$ is an aliphatically, cycloaliphatically or heteroaromatically-aliphatically substituted amino group, and the salts thereof, which can be used, for example, as antihypertensives.

The compounds of formula I are especially valuable intermediates in the preparation of δ-amino-γ-hydroxy-ω-aryl-alkanoic acid amides of formula IIc

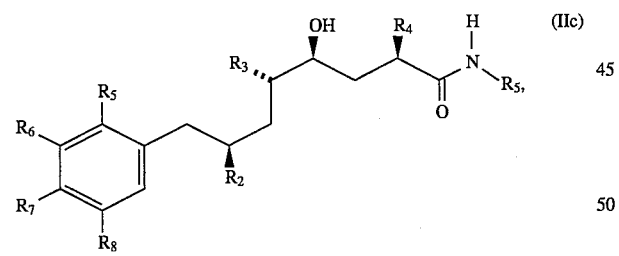

wherein $R_5$ is hydrogen, hydroxy, lower alkoxy, cycloalkoxy, lower alkoxy-lower alkoxy or free or esterified or amidated carboxy-lower alkoxy, $R_6$ is hydrogen, lower alkyl, cycloalkyl, lower alkoxy-lower alkyl, lower alkoxy-lower alkoxy-lower alkyl, cycloalkoxy-lower alkyl, hydroxy, optionally lower alkanoylated, halogenated or sulfonylated hydroxy-lower alkoxy; amino-lower alkyl that is unsubstituted or substituted by lower alkyl, lower alkanoyl and/or by lower alkoxycarbonyl; optionally hydrogenated heteroaryl-lower alkyl, lower alkoxyimino-lower alkyl; amino-lower alkoxy substituted by lower alkyl, lower alkanoyl and/or by lower alkoxycarbonyl; oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, optionally S-oxidised lower alkylthio-lower alkoxy, lower alkylthio(hydroxy)lower alkoxy, aryl-lower alkoxy, optionally hydrogenated heteroaryl-lower alkoxy, cyano-lower alkoxy, free or esterified or amidated carboxy-lower alkoxy or free or esterified or amidated carboxy-lower alkyl, $R_7$ is optionally halogenated lower alkyl, lower alkoxy-lower alkyl, cycloalkoxy-lower alkyl, hydroxy-lower alkyl, optionally S-oxidised lower alkylthio-lower alkyl, optionally hydrogenated heteroarylthio-lower alkyl, optionally hydrogenated heteroaryl-lower alkyl; amino-lower alkyl that is unsubstituted or N-mono- or N,N-di-lower alkylated, N-lower alkanoylated, N-lower alkanesulfonylated or N,N-disubstituted by lower alkylene, by unsubstituted or N'-lower alkylated or N'-lower alkanoylated aza-lower alkylene, by oxa-lower alkylene or by optionally S-oxidised thia-lower alkylene; cyano-lower alkyl, free or esterified or amidated carboxy-lower alkyl, cycloalkyl, aryl, hydroxy, lower alkoxy, cycloalkoxy, lower alkoxy-lower alkoxy, cycloalkoxy-lower alkoxy, hydroxy-lower alkoxy, aryl-lower alkoxy, optionally halogenated lower alkoxy, optionally S-oxidised lower alkylthio-lower alkoxy, optionally hydrogenated heteroaryl-lower alkoxy, optionally hydrogenated heteroarylthio-lower alkoxy; amino-lower alkoxy that is unsubstituted or N-mono- or N,N-di-lower alkylated, N-lower alkanoylated, N-lower alkanesulfonylated or substituted by lower alkylene, by unsubstituted or N'-lower alkylated or N'-lower alkanoylated aza-lower alkylene, by oxa-lower alkylene or by optionally S-oxidised thia-lower alkylene; cyano-lower alkoxy or free or esterified or amidated carboxy-lower alkoxy, or together with $R_8$ is lower alkylenedioxy or a fused-on benzo or cyclohexeno ring, $R_8$ together with $R_7$ is lower alkylenedioxy or a fused-on benzo or cyclohexeno ring, or is hydrogen, lower alkyl, hydroxy, lower alkoxy or cycloalkoxy, $R_2$ is lower alkyl or cycloalkyl, $R_6$ is unsubstituted or N-mono- or N,N-di-lower alkylated or N-lower alkanoylated amino, $R_4$ is lower alkyl, lower alkenyl, cycloalkyl or aryl-lower alkyl, and $R_6$ is lower alkyl, cycloalkyl, free or aliphatically esterified or etherified hydroxy-lower alkyl; amino-lower alkyl that is unsubstituted or N-lower alkanoylated, N-mono- or N,N-di-lower alkylated or N, N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N, N-di-lower alkylated thiocarbamoyl-lower alkyl, unsubstituted or N-mono- or N, N-di-lower alkylated sulfamoyl-lower alkyl, or a heteroaryl radical bonded via a carbon atom and optionally hydrogenated and/or oxo-substituted, or lower alkyl substituted by a heteroaryl radical bonded via a carbon atom and optionally hydrogenated and/or oxo-substituted, and the salts thereof, which are effective as renin inhibitors and can therefore be used as antihypertensives.

The compounds of formula I are very especially suitable for the preparation of compounds of formula IIa wherein $R_5$ and $R_8$ are hydrogen, $R_6$ is $C_1$–$C_4$alkoxy-$C_1$–$C_4$alkoxy, such as 3-methoxypropyloxy, or $C_1$–$C_4$alkoxy-$C_1$–$C_4$alkyl, such as 3-methoxybutyl, $R_7$ is $C_1$–$C_4$alkyl, such as isopropyl or tert-butyl, or $C_1$–$C_4$alkoxy, such as methoxy, $R_3$ is amino, $R_2$ and $R_4$ are branched $C_1$–$C_4$alkyl, such as isopropyl, and $R_6$ is carbamoyl-$C_1$–$C_4$alkyl, such as 2- or 3-carbamoylpropyl, 2-(3-carbamoyl)propyl or 1-(2-carbamoyl-2-methyl) propyl, N-$C_1$–$C_4$alkylcarbamoyl-$C_1$–$C_4$alkyl, such as 3-(N-methylcarbamoyl)propyl, 2-[1-(N-methylcarbamoyl)]propyl, 1-[2-(N-methylcarbamoyl)]propyl, especially 1-[2(R)-(N-methylcarbamoyl)]propyl, N,N-di-$C_1$–$C_4$alkylcarbamoyl-$C_1$–$C_4$alkyl, such as N,N-di-methylcarbamoylmethyl or 2-(N,N-dimethylcarbamoyl)ethyl,3-(N,N-dimethylcarbamoyl)-propyl, morpholino-$C_1$–$C_4$alkyl, such as 2-morpholinoethyl, 3-morpholinopropyl or 1-(2-morpholino-2-methyl) propyl, thiomorpholino-$C_1$–$C_4$alkyl, such as 2-thiomorpholinoethyl, 4-(1-$C_1$–$C_4$alkanoylpiperidyl)-$C_1$–$C_4$alkyl, such as 2-[4-(1-acetyl)piperidinyl]ethyl, 2-oxo-pyrrolidinyl-$C_1$–$C_4$alkyl, such as 2-oxopyrrolidin-5(S)-ylmethyl or 2-oxopyrrolidin-5(R)-yl-methyl, and the salts thereof.

The conversion of intermediates of formula I, especially of those wherein $R_3$ is azido, into renin inhibitors of formula II is carried out in customary manner, for example by converting a corresponding compound of formula I wherein $R_1$ is free or esterified carboxy, in customary manner, especially by conversion into the corresponding acid chloride, for example by reaction with oxalyl chloride, and subsequent reduction, for example using lithium tri-tert-butyloxyaluminium hydride in tetrahydrofuran, or converting a compound of formula I wherein $R_1$ is hydroxymethyl, by oxidation, for example using pyridine/sulfur trioxide in dimethyl sulfoxide/dichloro-methane, into the corresponding aldehyde of formula Ia

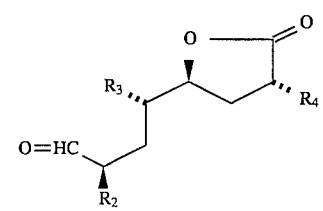

(Ia)

condensing the latter in customary manner, for example in tetrahydrofuran with cooling, for example at from −70° C. to −80° C., with a halomagnesium compound of the formula $R_A$-Mg-Hal (Ic), temporarily protecting the resulting compound of formula Id

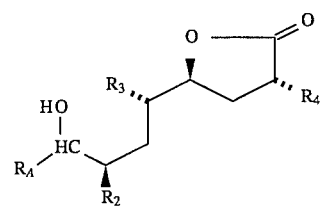

(Id)

at the hydroxy group, for example by reaction with acetic anhydride or isobutyric acid anhydride, especially in the presence of dimethylaminopyridine in dichloromethane, reacting the resulting compound of formula Ie

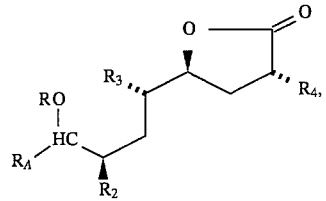

(Ie)

wherein R is a hydroxy-protecting group, for example acetyl or isobutyryl, with an amine of the formula H-$R_E$ (If), and hydrogenating the resulting compound of formula Ig

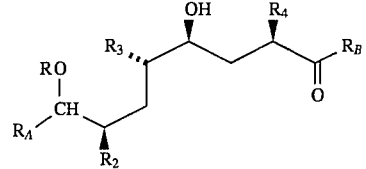

(Ig)

catalytically, for example in the presence of palladium, or preferably platinum oxide, on carbon at room temperature and normal pressure, the group R-O- optionally being replaced by hydrogen, and an azido group $R_3$ that maybe present being reduced to amino and the corresponding compound of formula IIa, IIb or IIc wherein $R_3$ is unsubstituted amino being obtained, which compound may then, if desired, be N-mono- or N,N-di-lower alkylated or N-lower alkanoylated.

The invention relates especially to compounds of formula I wherein $R_1$ is carboxy, lower alkoxycarbonyl, unsubstituted or lower alkyl-, lower alkoxy-, halo-and/or trifluoromethyl-substituted phenyl-lower alkoxycarbonyl, hydroxymethyl or formyl, $R_2$ and $R_4$ are each independently of the other lower alkyl radicals, lower alkenyl, lower alkoxy or lower alkylthio, 3- to 7-membered cycloalkyl-lower alkyl radicals, unsubstituted or lower alkyl-, lower alkoxy-, hydroxy-, halo-, nitro- and/or amino-substituted phenyl-lower alkyl or naphthyl-lower alkyl radicals or unsubstituted or lower alkyl-, lower alkoxy-, hydroxy-, halo-, nitro- and/or amino-substituted pyridyl-lower alkyl, indolyl-lower alkyl, quinolinyl-lower alkyl, pydmidinyl-lower alkyl, furyl-lower alkyl, benzofuranyl-lower alkyl or thienyl-lower alkyl, and $R_3$ is azido, lower alkylamino, di-lower alkylamino, lower alkanoylamino or N-lower alkanoyl-N-lower alkylamino, unsubstituted or lower alkyl-, lower alkoxy-, hydroxy-, halo-, nitro-and/or amino-substituted phenyl-lower alkylamino, N-lower alkyl-N-phenyl-lower alkyl-amino or N-lower alkanoyl-N-phenyl-lower alkyl-amino or N-lower alkoxycarbonylamino, N-lower alkyl-N-lower alkoxycarbonyl-amino, N-lower alkanoyl-N-lower alkoxycarbonyl-amino, N-lower alkoxycarbonyl-N-phenyl-lower alkylamino, N-phenyl-lower alkoxycarbonylamino, N-lower alkyl-N-phenyl-lower alkoxycarbonyl-amino, N-lower alkanoyl-N-phenyl-lower alkoxy-carbonyl-amino, N-phenyl-lower alkoxycarbonyl-N-phenyl-lower alkylamino, N-tri-lower alkylsilylamino, N-lower alkyl-N-tri-lower alkylsilyl-amino, N-lower alkanoyl-N-tri-lower alkyl-silyl-amino or N-tri-lower alkylsilyl-N-phenyl-lower alkylamino, and the salts thereof.

The invention relates especially, for example, to compounds of formula I wherein $R_1$ is carboxy, lower alkoxycarbonyl, hydroxymethyl or formyl, $R_2$ is lower alkyl, $R_3$ is azido, and $R_4$ is lower alkyl, or phenyl- or naphthyl-lower alkyl that is unsubstituted or mono-, di- or tri-substituted by lower alkyl, lower alkoxy, hydroxy, lower alkylamino, di-lower alkylamino, halogen and/or by trifluoromethyl, and the salts thereof.

The invention relates especially to compounds of formula I wherein $R_1$ is carboxy, $R_2$ and $R_4$ are $C_1$–$C_4$alkyl, preferably methyl or branched $C_1$–$C_4$alkyl, such as isopropyl, $C_2$–$C_4$alkenyl, such as allyl or methallyl, $C_1$–$C_5$alkoxy, such as methoxy, ethoxy, propyloxy, isopropyloxy, butyloxy, isobutyloxy, sec-butyloxy, tert-butyloxy or pentyloxy, $C_1$–$C_5$alkylthio, such as methylthio, ethylthio, propylthio, isopropylthio, butylthio, isobutylthio, sec-butylthio, tert-butylthio or pentylthio, 3- to 7-membered cycloalkyl-$C_1C_4$alkyl, such as cyclopropyl-, cyclobutyl-, cyclopentyl- or cyclohexyl-methyl, or phenyl-$C_1$–$C_4$alkyl that is unsubstituted or substituted by $C_1$–$C_4$alkyl, such as methyl, by $C_1$–$C_4$alkoxy, such as methoxy, by hydroxy, by halogen having an atomic number of up to and including 35, such as chlorine or bromine, by nitro and/or by amino, and $R_3$ is azido, $C_1$–$C_4$alkoxycarbonylamino or phenyl-$C_1$–$C_4$alkoxycarbonylamino, and the salts thereof.

The invention relates above all to compounds of formula I wherein $R_1$ is carboxy, $R_2$ is $C_1$–$C_4$alkyl, preferably methyl or branched $C_1$–$C_4$alkyl, such as isopropyl, $R_3$ is azido, and $R_4$ is $C_1$–$C_4$alkyl, preferably methyl or branched $C_1$–$C_4$alkyl, such as isopropyl, $C_2$–$C_4$alkenyl, such as allyl or methallyl, or phenyl-$C_1$–$C_4$alkyl that is unsubstituted or substituted by $C_1$–$C_4$alkyl, such as methyl, by $C_1$–$C_4$alkoxy, such as methoxy, by hydroxy, by halogen having an atomic number of up to and including 35, such as chlorine or bromine, by nitro and/or by amino, and the salts thereof.

The invention relates specifically to the compounds of formula I mentioned in the Examples and the salts thereof.

The process according to the invention for the preparation of compounds of formula I comprises, in a compound of formula III

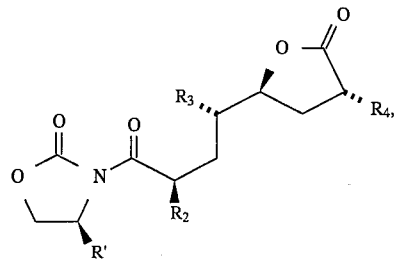

(III)

wherein

R' is an unsubstituted or substituted hydrocarbon radical, and $R_3$ is, for example, azido, $R_2$ and $R_4$ being as defined, hydrolysing the 4-R'-2-oxo-oxazolidin-1-ylcarbonyl group selectively to carboxy, reclosing with the use of an acid catalyst a lactone ring that may have opened, and, if desired, converting a compound of formula I according to the invention into a different compound of formula I according to the invention, separating a mixture of isomers which may be obtainable and/or converting the compound of formula I obtainable by the process into a salt or converting a salt obtainable by the process into the free compound or into a different salt.

Suitable hydrocarbon radicals are any desired aliphatic, cycloaliphatic, cycloaliphatic-aliphatic, araliphatic or aromatic hydrocarbon radicals, such as lower alkyl, lower alkenyl, 3-to 5-membered cycloalkyl, 3- to 5-membered cycloalkyl-lower alkyl, phenyl-lower alkyl, such as especially benzyl, naphthyl-lower alkyl, phenyl or naphthyl. Substituents, especially substituents of phenyl-lower alkyl, naphthyl-lower alkyl, phenyl or naphthyl, are, for example, lower alkyl, lower alkoxy, halogen, trifluoromethyl, nitro, amino or mono- or di-lower alkylamino.

The 4-R'-2-oxo-oxazolidin-1-ylcarbonyl group is hydrolysed, for example, by treatment with an alkali metal hydroxide in the presence of a basic hydrolysing agent, especially lithium hydroxide in the presence of hydrogen peroxide. Hydrogen peroxide is used, for example, in an approximately 10% by vol., for example from 7.5% by vol. to 12.5 % by vol., aqueous solution, in excess.

The reaction is carded out in customary manner, for example in a temperature range of from approximately −25° C. to approximately +10° C., especially from approximately −5° C. to approximately +5° C., advantageously in the presence of a water-miscible organic solvent that is inert towards hydrogen peroxide, such as a cyclic ether, especially tetrahydrofuran or dioxane. After decomposition of the excess hydrogen peroxide, for example using sodium hydrogen sulfite, working up is effected in customary manner.

Starting materials of formula III are prepared, for example, by reacting a 1,4-dihalobutene, for example 1,4-dibromobutene, first with a compound of formula IVa and then with a compound of formula IVb, or first with a compound of formula IVb and then with a compound of formula IVa

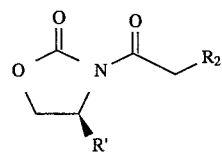

(IVa)

-continued

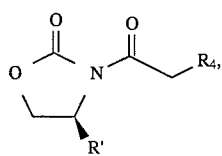
(IVb)

or in one step or stepwise with approximately twice the molar amount of a compound of formula IVa or IVb wherein R', $R_2$ and $R_4$ are as defined and converting the resulting compound of formula V

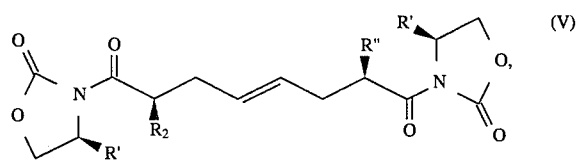
(V)

wherein R" is a radical $R_2$ or $R_4$, for example by treatment with a customary halogenating agent, such as elemental halogen, especially bromine or iodine, or preferably with an N-halosuccinimide, especially N-bromosuccinimide in 1,2-dimethoxyethane, into the corresponding compound of formula VI

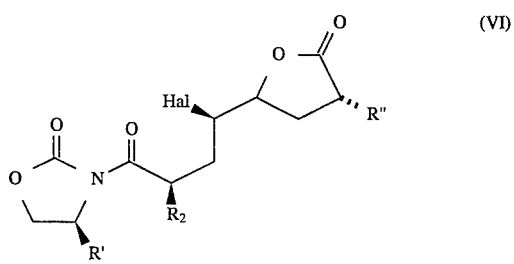
(VI)

wherein Hal is halogen, such as bromine, separating off the desired isomer wherein R" is $R_4$, replacing the halogen atom in that isomer by azido, for example by treatment with tetrabenzylammonium azide in toluene, with inversion, and, if desired, hydrogenating the azido group to amino and then aliphatically or araliphatically substituting the amino and/or protecting the amino with an amino-protecting group.

In a preferred form of the preparation of compounds of formula I wherein $R_3$ is azido, E-1,4-dibromobut-2-ene is reacted with at least twice the molar amount of a compound of formula IVa to form directly the corresponding compound of formula VI wherein R" is a group $R_4$. In that case the reaction of E-1,4-dibromobut-2-ene with a compound of formula IVa and the further reaction of the compound of formula V and the replacement of halogen by azido proceed substantially stereoselectively.

Compounds of formula I obtainable in accordance with the process can, if desired, be converted into different compounds of formula I.

For example, in compounds of formula I wherein $R_1$ is esterified carboxy, the esterified carboxy group can be converted into carboxy in customary manner, for example by basic or acid hydrolysis. Conversely, carboxy $R_1$ can be esterified in customary manner, for example by reaction with an alcohol in the presence of an acidic agent, or by conversion into chlorocarbonyl and further reaction with an alcohol in the presence of a basic condensation agent. If desired, an intermediate of formula III can be converted directly into a compound of formula I wherein $R_1$ is esterified carboxy by removing the 4-R'-2-oxo-oxazolidine group in the presence of suitable catalysts, such as titanium tetraisopropanolate.

It is also possible to reduce compounds of formula I wherein $R_1$ is esterified carboxy to the corresponding aldehyde wherein $R_1$ is formyl in customary manner, for example with dibutyl-aluminium hydride in toluene or by reaction with oxalyl chloride, and subsequent reduction, for example with sodium tri-tert-butyloxyaluminium hydride in tetrahydrofuran. Compounds of formula I wherein $R_1$ is carboxy can likewise be reduced to aldehydes by reaction with a chloroformic acid ester and subsequent reduction of the mixed anhydride formed, for example with sodium boranate.

Furthermore, in resulting compounds of formula I wherein $R_3$ is azido, the azido group can be reduced to amino catalytically, for example in the presence of palladium on carbon at room temperature and normal pressure, and the amino group can be N-mono- or N,N-di-lower alkylated or N-lower alkanoylated.

It is also possible for salts of compounds of formula I obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is formed under the process conditions and further processed in situ. It is preferable to use those starting materials which result in the compounds described above as being very preferred or very especially preferred.

The invention relates also to novel starting materials, which have been developed specifically for the preparation of the compounds according to the invention, especially the group of starting materials resulting in the compounds of formula I described at the beginning as being preferred, to processes for their preparation and to their use as intermediates.

This relates especially to compounds of formulae III, V and VI which, as mentioned, are suitable as intermediates in the preparation of compounds of formula I.

The invention relates accordingly also to compounds of formulae III, V and VI

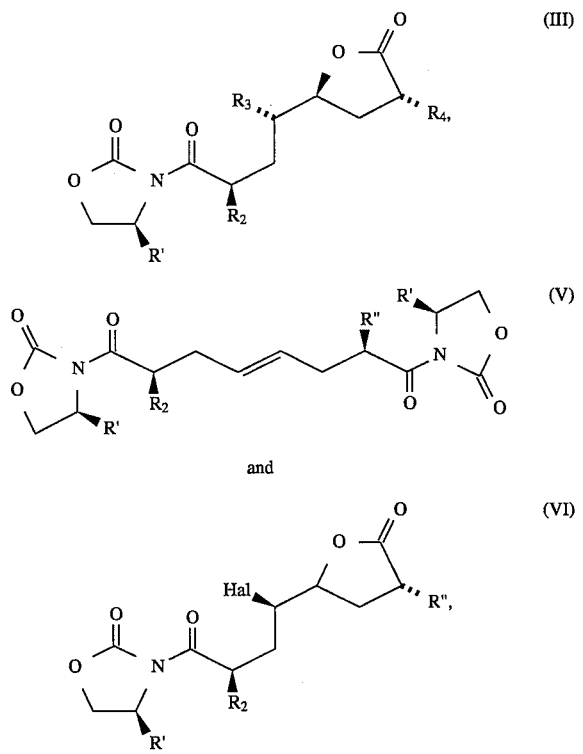

wherein $R_2$, $R_4$ and R" are each independently of the others aliphatic, cycloaliphatic-aliphatic, araliphatic or heteroarylaliphatic radicals, $R_3$ is azido, or amino that is aliphatically or araliphatically substituted and/or protected by an amino-protecting group, R' is an aliphatic, cycloaliphatic or cycloaliphatic-aliphatic hydrocarbon radical, or an araliphatic or aromatic hydrocarbon radical that is unsubstituted or substituted by lower alkyl, lower alkoxy, halogen, trifluoromethyl, nitro, amino and/or by mono- or di-lower alkylamino, and Hal is halogen, and to the salts thereof, to processes for the preparation thereof and to the use thereof as intermediates in the preparation of medicinal active ingredients.

In the compounds of formulae III, V and VI prepared in accordance with the invention, the variable $R_2$ is preferably as defined under formula I, the variable R' is preferably as defined under formula III, the variable R" is preferably as defined under formula I for $R_2$ or $R_4$, and Hal is preferably halogen having an atomic number of up to and including 35.

The invention relates above all to compounds of formulae III, V and VI wherein $R_2$, $R_4$ and R" are each independently of the others lower alkyl, lower alkenyl, lower alkoxy or lower alkylthio, 3- to 7-membered cycloalkyl-lower alkyl radicals, unsubstituted or lower alkyl-, lower alkoxy-, hydroxy-, halo-, nitro- and/or amino-substituted phenyl-lower alkyl or naphthyl-lower alkyl radicals, or unsubstituted or lower alkyl-, lower alkoxy-, hydroxy-, halo-, nitro- and/or amino-substituted pyridyl-lower alkyl, indolyl-lower alkyl, quinolinyl-lower alkyl, pyrimidinyl-lower alkyl, furyl-lower alkyl, benzofuranyl-lower alkyl or thienyl-lower alkyl, $R_3$ is azido, lower alkylamino, di-lower alkylamino, lower alkanoylamino or N-lower alkanoyl-N-lower alkylamino, unsubstituted or lower alkyl-, lower alkoxy-, hydroxy-, halo-, nitro-and/or amino-substituted phenyl-lower alkylamino, N-lower alkyl-N-phenyl-lower alkyl-amino or N-lower alkanoyl-N-phenyl-lower alkyl-amino or N-lower alkoxycarbonylamino, N-lower alkyl-N-lower alkoxycarbonyl-amino, N-lower alkanoyl-N-lower alkoxycarbonyl-amino, N-lower alkoxycarbonyl-N-phenyl-lower alkylamino, N-phenyl-lower alkoxycarbonylamino, N-lower alkyl-N-phenyl-lower alkoxycarbonyl-amino, N-lower alkanoyl-N-phenyl-lower alkoxycarbonyl-amino, N-phenyl-lower alkoxycarbonyl-N-phenyl-lower alkylamino, N-tri-lower alkylsilylamino, N-lower alkyl-N-tri-lower alkylsilyl-amino, N-lower alkanoyl-N-tri-lower alkylsilyl-amino or N-tri-lower alkylsilyl-Nophenyl-lower alkylamino, and R" is lower alkyl, lower alkenyl, 3- to 5-membered cycloalkyl, 3- to 5-membered cycloalkyl-lower alkyl, phenyl-lower alkyl that is unsubstituted or substituted in the phenyl moiety by lower alkyl, lower alkoxy, halogen, trifluoromethyl, nitro, amino and/or by mono- or di-lower alkylamino, naphthyl-lower alkyl that is unsubstituted or substituted in the naphthyl moiety by lower alkyl, lower alkoxy, halogen, trifluoromethyl, nitro, amino and/or by mono- or di-lower alkylamino, or phenyl or naphthyl that is unsubstituted or substituted by lower alkyl, lower alkoxy, halogen, trifluoromethyl, nitro, amino and/or by mono- or di-lower alkylamino, and the salts thereof.

The invention relates especially to compounds of formulae III, V and VI wherein $R_2$, $R_4$ and R" are $C_1$–$C_4$alkyl, preferably methyl or branched $C_1$–$C_4$alkyl, such as isopropyl, $C_2$–$C_4$alkenyl, such as allyl or methallyl, $C_1$–$C_5$alkoxy, such as methoxy, ethoxy, propyloxy, isopropyloxy, butyloxy, isobutyloxy, sec-butyloxy, tert-butyloxy or pentyloxy, $C_1$–$C_5$alkylthio, such as methylthio, ethylthio, propylthio, isopropylthio, butylthio, isobutylthio, sec-butylthio, tert-butylthio or pentylthio, 3- to 7-membered cycloalkyl-$C_1$–$C_4$alkyl, such as cyclopropyl-, cyclobutyl-, cyclopentyl- or cyclohexyl-methyl, or phenyl-$C_1$–$C_4$alkyl that is unsubstituted or substituted by $C_1$–$C_4$alkyl, such as methyl, by $C_1$–$C_4$alkoxy, such as methoxy, by hydroxy, by halogen having an atomic number of up to and including 35, such as chlorine or bromine, by nitro and/or by amino, R' is phenyl-$C_1$–$C_4$alkyl that is unsubstituted or substituted by $C_1$–$C_4$alkyl, such as methyl, by $C_1$–$C_4$alkoxy, such as methoxy, by hydroxy, by halogen having an atomic number of up to and including 35, such as chlorine or bromine, by nitro and/or by amino, Hal is halogen having an atomic number of up to and including 35, such as chlorine or bromine, and $R_3$ is azido, and the salts thereof.

The invention relates above all to compounds of formulae III, V or VI wherein $R_2$ is $C_1$–$C_4$alkyl, preferably methyl or branched $C_1$–$C_4$alkyl, such as isopropyl, $R_4$ and R" are $C_1$–$C_4$alkyl, preferably methyl or branched $C_1$–$C_4$alkyl, such as isopropyl, $C_2$–$C_4$alkenyl, such as allyl or methallyl, or phenyl-$C_1$–$C_4$alkyl that is unsubstituted or substituted by $C_1$–$C_4$alkyl, such as methyl, by $C_1$–$C_4$alkoxy, such as methoxy, by hydroxy, by halogen having an atomic number of up to and including 35, such as chlorine or bromine, by nitro and/or by amino, R' is benzyl, Hal is halogen having an atomic number of up to and including 35, such as chlorine or bromine, and $R_3$ is azido, and the salts thereof.

The process according to the invention for the preparation of compounds of formulae III, V and VI comprises:

a) for the preparation of compounds of formula V, reacting a 1,4-dihalobutene, for example 1,4-dibromobutene, first with a compound of formula IVa and then with a compound of formula IVb, or first with a compound of formula IVb and then with a compound of formula IVa

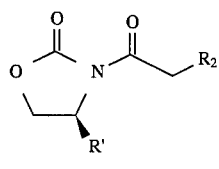 (IVa)

or

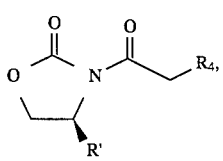 (IVb)

or in one step or stepwise with approximately twice the molar amount of a compound of formula IVa or IVb wherein R', $R_2$ and $R_4$ are as defined, or b) for the preparation of compounds of formula VI, treating a compound of formula V

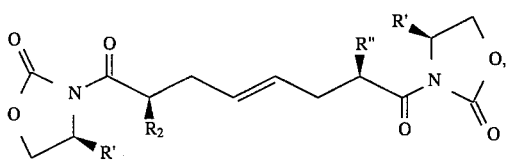 (V)

wherein R" is a radical $R_2$ and $R_4$, with a customary halogenating agent, such as elemental halogen, especially bromine or iodine, or preferably with an N-halosuccinimide, especially N-bromosuccinimide in 1,2-dimethoxyethane, and separating off the desired isomer wherein R" is $R_4$, and/or c) for the preparation of compounds of formula III, in a compound of formula VI

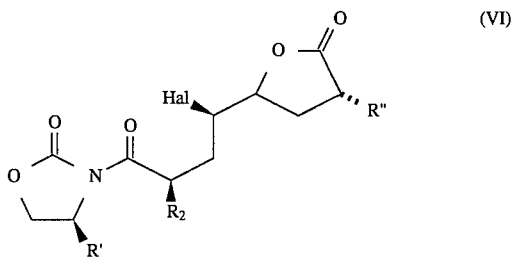 (VI)

wherein Hal is halogen, such as bromine, replacing the halogen atom by azido, for example by treatment with tetrabenzylammonium azide in toluene, with inversion, and, if desired, hydrogenating the azido group to amino and then aliphatically or araliphatically substituting the amino and/or protecting the amino with an amino-protecting group, and, if desired, converting a compound of formula III, V or VI according to the invention into a different compound of formula III, V or VI according to the invention, separating a mixture of isomers which may be obtainable and/or converting the compound of formula III, V or VI obtainable by the process into a salt or converting a salt obtainable by the process into the free compound or into a different salt.

The following Examples serve to illustrate the invention; temperatures are given in degrees Celsius, pressures in mbar.

The abbreviation "$R_f(A)$" means, for example: that the Rf value was determined in solvent system A. The quantity ratio of solvents to one another is always given in parts by volume.

The same abbreviations are used for indicating the eluant systems for flash chromatography and medium pressure chromatography.

Mass-spectroscopic measurements are obtained either by conventional MS or in accordance with the "Fast-Atom-Bombardment" (FAB-MS) method. In the former case the mass data relate to the unprotonated molecule ion $(M)^+$ or the protonated molecule ion $(M+H)^+$.

The short names and abbreviations used have the following meanings:

| | |
|---|---|
| $C_{18}$-Nucleosil ® | brand name for reversed phase column material for HPLC charged with octadecyl radicals (Nucleosil ® 5$C_{18}$, Macherey & Nagel, FRG) |
| HPLC - column dimensions: | 250 × 4.6 mm |
| HPLC - column packing: | Nucleosil ® 5$C_{18}$ |
| HPLC - eluants: | A) water + 0.1% by vol. trifluoroacetic acid B) acetonitrile + 0.1% by vol. trifluoroacetic acid |
| HPLC - gradient O: | 20–100% B in 20 minutes + 8 minutes 100% B |
| HPLC - gradient I: | linear in 60 minutes from 30% by vol. B + 70% by vol. A to 90% by vol. B + 10% by vol. A |
| pFAB-MS | Fast-Atom-Bombardment mass spectroscopy |
| FC | flash chromatography |
| HPLC | high performance liquid chromatography |
| Hyflo ® | brand name for filter aids (Fluka, Buchs, Switzerland) |
| IR | infrared spectroscopy |
| b.p. | at the pressure indicated in torr |
| ml | millilitres |
| MS | mass spectroscopy |

| | |
|---|---|
| $R_f$ | ratio of the migration of a substance to the distance of the eluant front from the starting point in TLC |
| $R_t$ | retention time of a substance in HPLC (in minutes) |
| m.p. | melting point (temperature). |

EXAMPLE 1: 2(S)-[2(S)-Azido-2(S)-(4(S)-isopropyl-5-oxo-tetrahydrofuran-2(S)-yl)-ethyl]-3-methyl-butyric acid To a solution, stirred at −5° C., of 55.3 g of 3-{2(S)-[2(S)-azido-2(S)-(4(S)-isopropyl-5-oxo-tetrahydrofuran-2(S)-yl)-ethyl]-3-methyl-butyryl}-4(S)-benzyl-oxazolidin-2-one in 500 ml of tetrahydrofuran there are slowly added in succession 175 ml of water, 74 ml of 30% hydrogen peroxide solution and 5.9 g of lithium hydroxide. The reaction mixture is stirred further for 1 hour at 5° C. and for 150 minutes at room temperature, and then at 3° C. 750 ml of aqueous 1M sodium sulfite solution are added in the course of 30 minutes and the reaction mixture is stirred further for 30 minutes at room temperature. The reaction mixture is then freed of tetrahydrofuran by concentration and the aqueous solution is washed three times with 1200 ml of ethyl acetate, the organic phases being back-extracted three times with 100 ml of 0.1N sodium hydroxide. The combined aqueous phases are adjusted to pH 1–2 with approximately 200 ml of 4N hydrochloric acid and extracted three times with 1200 ml of ethyl acetate. The organic phases are combined, dried over magnesium sulfate and concentrated by evaporation to yield the crude product which, in order to cyclise opened lactone, is dissolved in 500 ml of toluene and, together with approx. 1 g of molecular sieve and approx. 1 g of p-toluenesulfonic acid, is stirred for 2 hours at 50° C. Filtration, concentration by evaporation and purification of the residue by means of FC (hexane/ethyl acetate/ glacial acetic acid 30:60:1) yields the title compound which crystallises spontaneously: m.p. 56°–58° C.; $R_f$ (hexane/ ethyl acetate/glacial acetic acid 30:60:1)=0.62.

The 3-{2(S)-[2(S)-azido-2(S)-(4(S)-isopropyl-5-oxo-tetrahydrofuran-2(S)-yl)-ethyl]-3-methyl- butyryl}-4(S)-benzyl-oxazolidin-2-one used as starting material can be prepared, for example, as follows:

a) trans- 1,8-bis [4(S)-benzyl-2-oxo-oxazolidin-3-yl]-2(S),7(S)-diisopropyl-oct-4-ene-1,8-dione With stirring at −75° C., 48 ml of a 1.0M solution of lithium hexamethyldisilazide in tetrahydrofuran are added dropwise in the course of 1 hour to a solution of 11.5 g of 4(S)-benzyl-3-isovaleroyl-oxazolidin-2-one in 32 ml of tetrahydrofuran. The reaction mixture is stirred further for 2 hours at −75° C. and for 20 minutes at −20° C., then 10 ml of 1,3-dimethyl-3,4,5,6-tetrahydro- -2-(1H)-pyrimidone (DMPU) and, in the course of 45 minutes, a solution of 4.28 g of 1,4-dibromo-2-butene in 10 ml of tetrahydrofuran are added thereto. The reaction mixture is stirred further for 15 hours at −20° C., and then in the course of 1 hour brought to 0° C. At −20° C., 10 ml of saturated ammonium chloride solution are then added thereto and after 15 minutes the reaction mixture is brought to room temperature. The reaction mixture is then partitioned between dichloromethane and saturated sodium chloride solution/water (1:1). The organic phases are combined, dried over sodium sulfate and concentrated by evaporation and the residue is purified by means of FC (hexane/ethyl acetate 4:1) to yield the title compound: Rf (hexane/ethyl acetate 4:1)=0.30; m.p.= 110°–111° C. (crystallised from ethyl acetate/hexane).

b) 4(S)-Benzyl-3-{2(S)-[2(R)-bromo-2(R)-(4(S)-isopropyl-5-oxo-tetrahydrofuran-2(S)-yl)-ethyl]-3-methyl-butyryl}-oxazolidin-2-one 10.5 g of N-bromosuccinimide are added, with stirring, to a solution of 30 g of trans-1,8-bis-[4(S)-benzyl-2-oxo-oxazolidin-3-yl]-2(S),7(S)-diisopropyl-oct-4-ene-1,8-dione in 360 ml of tetrahydrofuran and 120 ml of water, the temperature being maintained at room temperature using an ice bath. The reaction mixture is stirred further for 2 hours at room temperature and then the tetrahydrofuran is evaporated off using a rotary evaporator. The aqueous residue is partitioned between diethyl ether (twice 200 ml), water (twice 50 ml) and saturated sodium chloride solution (once 50 ml). The organic phases are combined, dried over magnesium sulfate and concentrated by evaporation and the residue is purified by means of FC (90 g of silica gel, hexane/ethyl acetate 3:1) to yield the title compound in the form of a crude product. Crystallisation from diisopropyl ether yields the pure compound: m.p.=91/92° C.; $R_f$ (hexane/ethyl acetate 8:2)=0.28.

c) 3-{2(S)-[2(S)-Azido-2(S)-(4(S)-isopropyl-5-oxo-tetrahydrofuran-2(S)-yl)-ethyl]-3-methyl-butyryl}-4(S)-benzyl-oxazolidin-2-one 13.6 g of freshly dried tetrabutylammonium azide are added to a solution, stirred at room temperature, of 17.8 g of 4(S)-benzyl-3-{2(S)-[2(R)-bromo-2(R)-(4(S)-isopropyl-5-oxo- tetrahydrofuran-2(S)-yl)-ethyl]-3-methyl-butyryl}-oxazolidin-2-one in 180 ml of toluene and in the course of 160 hours' stirring at room temperature a further 10 g of the azide is added thereto. The reaction mixture is then partitioned between ethyl acetate and water (twice) and saturated sodium chloride solution (once). The organic phases are combined, dried over sodium sulfate and concentrated. The title compound is obtained from the residue by means of FC (hexane/ethyl acetate 8:2) and crystallisation from diethyl ether/hexane: m.p.=102°–103° C.; $R_f$ (hexane/ethyl acetate 8:2)=0.2.

EXAMPLE 2: Alternative preparation of 2-(S)-[2(S)-azido-2(S)-(4(S)-isopropyl-5-oxo- tetrahydrofuran-2(S)-yl)-ethyl]-3-methyl-butyric acid In a sulfonating flask, 53.8 g (0.118 mol) of 3-{2(S)-[2(S)-azido-2(S)-(4(S)-isopropyl-5-oxo-tetrahydrofuran-2(S)-yl)-ethyl]-3-methyl-butyryl}-4(S)-benzyl-oxazolidin-2-one are dissolved in a mixture of tetrahydrofuran (215 ml) and water (215 ml) and cooled to 0°–5° C. With stirring, first a 30 % hydrogen peroxide solution (73.0 ml)is added dropwise in the course of 10 minutes and then lithium hydroxide (5.60 g) is added in one portion. The temperature of the white suspension is allowed to rise to room temperature and the suspension is then stirred for 2 hours. The reaction mixture is cooled to 0°–5° C. and a 1M sodium sulfite solution (600 ml) is added dropwise in the course of 30 minutes. After 30 minutes stirring, the test for peroxides (Merckoquant® peroxide test) remains negative. The reaction mixture is concentrated using a rotary evaporator, removing tetrahydrofuran, and the alkaline aqueous phase (approx. 900 ml) is then extracted with ethyl acetate (3×200 ml). The combined organic phases are back-extracted with 0.1N sodium hydroxide solution (1×30 ml), washed with saturated sodium chloride solution (1×60 ml), dried over magnesium sulfate, filtered and concentrated. The crude 4-(S)-benzyl-1,3-oxazolidin-2-one is obtained in the form of a white-beige solid (23.0 g crude,>100 %). The alkaline aqueous phases obtained in the first part of the working-up are combined, adjusted to pH 1–2 by the addition of 4N hydrochloric acid and extracted with ethyl acetate (4×250 ml), and the organic phases are washed with saturated sodium chloride solution (1×60 ml), dried over magnesium sulfate, filtered and concentrated. The pale yellow oil (48.3 g) thus obtained is dissolved in toluene (500 ml) and a catalytic amount of p-toluenesulfonic acid monohydrate (110 mg) is added thereto and the product is stirred over a period of 20 minutes at 40° C. The clear solution is concentrated using a rotary evaporator and the residue is dried overnight under a high vacuum. The crude title compound is obtained in the form of a pale yellow oil (34.0 g, 97%) that slowly crystallises at room temperature. $R_f$ (hexane/ethyl acetate/glacial acetic acid 50:50:1 )=0.44.

In a modification of the process according to Example 1, the 3-{2(S)-[2(S)-azido-2(S)-(4(S)-isopropyl-5-oxo- tetrahydrofuran-2(S)-yl]-ethyl]-3-methyl-butyryl]-4(S)-benzyl-oxazolidin-2-one used as starting material can also be prepared as follows:

a) trans-1,8-bis[4(S)-benzyl-2-oxo-oxazolidin-3-yl]-2(S), 7(S)-diisopropyl-oct-4-ene- 1,8-dione Over a period of 1 hour, a 1M lithium hexamethyldisilazane solution (39.2 ml) in tetrahydrofuran is added dropwise at 0° C. under argon to a solution of 4(S)-N-isovaleroyl-4-benzyl-oxazolidin-2-one (10.0 g) in tetrahydrofuran (26 ml), the reaction temperature being maintained at below 3° C. When the addition is complete, the mixture is stirred for 2 hours at 0° C. Then 1,3-dimethyl-3,4,5,6-tetrahydro-2(1 H)-pyrimidinone (9.4 ml) and a solution of trans-1,4-dibromo-2-butene (4.0 g) in tetrahydrofuran (15.4 ml) are added and the solution is stirred for 18 hours at 0° C. Finally, the reaction is quenched by the slow addition of a saturated aqueous ammonium chloride solution (30 ml). The reaction mixture is diluted with diethyl ether (500 ml), the organic phase is washed with water (2×100 ml), the aqueous phases are back-extracted with diethyl ether (2×100ml), and the combined organic phases are washed with saturated sodium chloride solution (2×100 ml), dried over sodium sulfate and concentrated in vacuo. The crude product (14.9 g) is recrystallised from methanol and the title compound (8.41 g) is obtained in the form of a white powder. M.p. 108°–109° C. (m.p. 110°–111° C. from diethyl ether/hexane). $[\alpha]^{25}_D$=+75.5±1.0(c1, $CH_2Cl_2$). $^1$H-NMR (500 MHz, DMSO-$d_6$): δ0.84 (d,J=6.8 Hz,6H), 0.87 (d, J=6.8 Hz, 6H), 1.87 (m,2H), 2.23 (m,2H), 2.34 (m,2H), 2.84 (dd,J=8.2, 13.5 Hz, 2H), 3.01 (dd,J=3, 13.5 Hz, 2H), 3.66 (m,2H), 4.13 (dd,J=2.7, 8.8 Hz,2H), 4.30 (t,J=8.5 Hz,2H), 4.67 (m,2H), 546 (m,2H), 7.2–7.3 (m, 10H) ppm. Anal.: $C_{34}H_{42}N_2O_6$(574.72):calc.: C=71.06%, H=7.37%, N=4.87 %; found: C=71.20%; H=7.40%; N=4.90%.

b) 4(S)-Benzyl-3-{2(S)-[2(R)-bromo-2(R)-(4(S)-isopropyl-5-oxo-tetrahydrofuran-2(S)-yl]-ethyl]-3-methyl-butyryl}-oxazolidin-2-one The product (50.0 g) obtained by the method described in a) is dissolved in dichloromethane (1 l). After the addition of water (250 ml), the two-phase mixture is stirred at room temperature for 30 minutes. Then N-bromosuccinimide (17 g) is added in one portion and the batch is stirred for 15 minutes. The batch is then heated to 35° C. and stirred thoroughly at that temperature for 24 hours. After cooling to room temperature the two phases are separated, the aqueous phase is extracted with dichloromethane (200 ml) and the combined organic phases are washed with 0.1N sodium thiosulfate solution (250 ml) and water (250 ml). The aqueous phases are each back-extracted once with ethyl acetate. After concentration of the solvent and drying under a high vacuum the crude product is obtained in the form of a slightly yellowish viscous oil (62 g). Recrystallisation from a 4:1 mixture of isopropanol/water (200 ml) yields the title compound in the form of a white crystalline solid (33 g, 77%). M.p. 91°∝93° C. $[\alpha]^{25}_D$=+38.6±1.0 (c1, $CH_2Cl_2$). $^1$H-NMR (500 MHz, DMSO-$d_6$); δ0.85 (d,J=6.8 Hz, 3H), 0.86 (d,J=6.9 Hz, 3H), 0.93 (d,J=6.9 Hz, 3H), 0.95 (d,J=6.9 Hz, 3H), 1.93 (m, 1H), 2.01 (m, 1H), 2.1–2.3 (m, 4H), 2.72 (m, 1H), 2.83 (dd,J=8.8, 13.4 Hz, 1H), 3.14 (dd,J=3, 13.4 Hz, 1H), 3.89 (m, 1H), 4.15 (dd, J=2.4, 8.8 Hz, 1H), 4.31 (t,J=8.6 Hz, 1H), 4.40 (m, 1H), 4.6–4.7 (m, 2H), 7.2–7.3 (m, 5H) ppm. Anal. $C_{24}H_{32}BrNO_5$ (494.43): calc. C=58.30%, H=6.52%, N=2.83%, Br=16.16%; found: C=58.09%; H=6.61%; N=2.72%, Br=16.21%.

The mother liquid that is obtained is concentrated in vacuo at 50° C. with azeotropic removal of residual water. With stirring at room temperature, methyl tert-butyl ether (125 ml) is added to the resulting oily residue (25 g), whereupon crystallisation begins. After 30 minutes, hexane (200 ml) is added and the reaction mixture is stirred for a further 30 minutes at room temperature. The precipitate is filtered off, washed with a 1:2 mixture of methyl tert-butyl ether/hexane (15 ml) and dried. 4(S)-Benzyl-1,3-oxazolidin-2-one is obtained in the form of a white crystalline solid (13.6 g, 88%), m.p. 86°–88° C.

c1) 3-{2(S)-[2(S)-Azido-2(S)-(4(S)-isopropyl-5-oxo-tetrahydrofuran-2(S)-yl]-ethyl]-3-methyl-butyryl}-4(S)-benzyl-oxazolidin-2-one The product (66.0 g) obtained by the method described in b) and tricaprylylmethyl-ammonium chloride (2.67 g) are dissolved in toluene (1 l) and, with stirring, a solution of sodium azide (34.7 g) in water (100 ml) is added thereto. The emulsion is stirred for 48 hours at 76° C (oil bath 100° C.) and then cooled to room temperature. The two phases are separated, the aqueous phase is extracted with toluene (100 ml) and the combined organic phases are washed with water (2×100 ml). Concentration of the solvent and drying under a high vacuum yields the crude product (70.1 g) in the form of a yellowish oil. After crystallisation from a 1:1 mixture of methyl tert-butyl ether/hexane (560 ml), the precipitate is filtered, washed with an ice-cold 1:1 mixture of methyl tert-butyl ether/hexane (2×15 ml) and dried at 50° C. under a high vacuum. The title compound is obtained in the form of a white crystalline solid (46 g, 75%). M.p. 104°–105° C. IR (KBr) 2980, 2100, 1775 (broad double band), 1695, 1385, 1345, 1190 $cm^{-1}$. $^1$H-NMR (500 MHz, DMSO-$d_6$): δ0.82 (d, J=6.9 Hz, 3H), 0.87 (d,J=6.8 Hz, 3H), 0.92 (d,J=6.8 Hz, 3H), 0.95 (d,J=6.8Hz, 3H), 1.52 (m, 1H), 1.94 (m, 1H), 1.95–2.1 (m, 2H), 2.18 (m, 1H), 2.66 (m, 1H), 2.90 (dd,J= 8.3, 13.4 Hz, 1H), 3.10 (dd, J=3.4, 13.4 Hz, 1H), 3.38 (m, 1H), 3.86 (m, 1H), 4.17 (dd,J=2.4, 8.8 Hz, 1H), 4.34 (t, J=8.6 Hz, 1H), 4.34 (m, 1H), 4.48 (m, 1H), 4.71 (m, 1H), 7.2–7.3 (m, 5H) ppm. $[\alpha]^{25}_D$=+35.2±1.0 (c 1, $CH_2Cl_2$). Anal.: $C_{24}H_{32}N_4O_5$ (456.54): ca.: C=63.14%, H=7.06%, N=12.27%; found: C=62.94%; H=7.12%; N=12.08%.

c2) Alternative preparation of 3-{2(S)-[2(S)-azido-2(S)-(4(S)-isopropyl-5-oxo-tetrahydrofuran-2(S)-yl]-ethyl]-3-methyl-butyryl}-4(S)-benzyl-oxazolidin-2-one Tetrabutylammonium azide (0.69 g; prepared by the method described by M. De Giorgi et al. in Synth. Commun. (1987), 17, 521–533) is added to a solution of the product of b) (1.0 g) in toluene (15 ml) at room temperature and the batch is stirred at 50° C. for 12 h. The reaction mixture is cooled and diluted with ethyl acetate, and the organic phase is washed with water, dried over sodium sulfate and concentrated. Recrystallisation of the residue from diisopropyl ether yields the title compound in the form of a crystalline solid (0.51 g, 56%).

EXAMPLE 3: Alternative preparation of 2(S)-[2(S)-azido-2(S)-(4(S)-isopropyl-5-oxo-tetrahydrofuran-2(S)-yl)-ethyl]-3-methyl-butyric acid With stirring at 0°–5° C., a 30% hydrogen peroxide solution (67 ml) is added dropwise over a period of 15 minutes to a solution of the product from Example 2c) (50.0 g) in tetrahydrofuran (250 ml) and water (125 ml) and then lithium hydroxide (7.85 g) is added in one portion thereto. The temperature of the reaction mixture is allowed to rise to room temperature and stirring is continued for a further 3 hours. The reaction mixture is cooled to 5°–10° C., and 2M sodium sulfite solution is added dropwise until the test for peroxide (Merckoquant® peroxide test) remains negative (190 ml of a 2M sodium sulfite solution). The reaction batch is washed with ethyl acetate (3×100 ml) and the combined organic phase is back-extracted with 0.1N sodium hydroxide solution. The combined alkaline aqueous phase is adjusted to pH 4-5 with 4N hydrochloric acid and extracted with ethyl acetate (3×100 ml). Toluene (100 ml) is added to the combined organic phases which are then concentrated slowly using a rotary evaporator. The crude title compound is obtained in the form of a colourless oil (31.6 g, 97%). Recrystallisation from hexane/diethyl ether yields an analytically pure product: m.p. 58°–60° C. IR ($CH_2Cl_2$) 3500 (w), 2965, 2110, 1775, 1745 (w), 1705, 1180 $cm^{-1}$. $[\alpha]^{25}_D$= /23.4±1.0 (c1, $CH_2Cl_2$). $^1$H-NMR (300 MHz, $CD_3OD$): δ0.92 (d,J=6.9 Hz, 3H), 0.95 (d,J=6.8 Hz, 6H), 1.04 (d,J=6.9 Hz, 3H), 1.64 (m, 1H), 1.85 (m, 1H), 1.95 (m, 1H), 2.05–2.3 (m, 3H), 2.42 (ddd, J=3, 6.5, 11.6 Hz, 1H), 2.70 (ddd, J=5.2, 6.8, 10.2 Hz, 1H), 3.36 (ddd, J=2.6, 5.6, 11.1 Hz, 1H), 4.48 (ddd, J=5.6, 5.6, 8.2 Hz, 1H) ppm. $C_{14}H_{23}N_3O_4$(297.36): calc.: C=56.54%, H=7.79%, N=14.13%; found: C=56.76%; H=7.71%; N=13.81%.

EXAMPLE 4: 2-{2(S)-Azido-2-[4(S)-isopropyl-5-oxo-tetrahydrofuran-2(S)-yl]-ethyl}-3(S)-methyl-butyraldehyde With stirring at 0° C., 1.45 ml of oxalyl chloride are added dropwise in the course of 10 minutes to a solution of 1.7 g of 2(S)-[2(S)-azido-2(S)-(4-(S)-isopropyl-5-oxo-tetrahydrofuran-2(S)-yl) -ethyl]-3-methyl-butyric acid in 20 ml of toluene. 0.03 ml of N,N-dimethylformamide is then added and the temperature is increased in the course of 30 minutes to 37° C. The reaction mixture is stirred for 2 hours at 37° C., then clarified by filtration and then, under reduced pressure and at a bath temperature of 30° C., carefully highly concentrated (avoiding full concentration by evaporation!). The residue is twice more dissolved in 10 ml of toluene and concentrated again in the same manner. The crude acid chloride thus obtained is dissolved in 5 ml of tetrahydrofuran, and at –75° C. 16 ml of a 0.34M solution of NaAlH(O-tert-Bu)$_3$ in diglyme are added thereto in the course of 30 minutes. The reaction mixture is further stirred for 70 minutes at –75° C. and then at the same temperature a solution of 0.385 ml of glacial acetic acid in 1 ml of tetrahydrofuran is added dropwise thereto, followed by 2.1 ml of saturated ammonium chloride solution and 20 ml of diethyl ether. The batch is brought to room temperature and partitioned between diethyl ether and water/saturated sodium chloride solution. The organic phases are combined, dried over magnesium sulfate and concentrated by evaporation, and the residue is purified by means of FC (hexane/ethyl acetate=95:5) to yield the title compound: $R_f$ (hexane/ethyl acetate=2:1)=0.55; HPLC $R_t$=16.4 minutes.

EXAMPLE 5: 2-{2(S)-Azido-2-[4(S)-isopropyl-5-oxo-tetrahydrofuran-2(S)-yl]-ethyl}-3(S)-methyl-butanol To a solution of 8.0 g of 2(S)-[2(S)-azido-2(S)-(4(S)-isopropyl-5-oxo-tetrahydrofuran-2(S)-yl)- ethyl]-3-methyl-butyric acid (crude product from Example 2 or 3) in anhydrous tetrahydrofuran (180 ml) there are added dropwise in succession at –10° C. triethylamine (5.62 ml) and chloroformic acid methyl ester (2.59 ml). The white suspension is then stirred first at –10° C. for 1 hour and then at 0° C. over a period of 2 hours. The batch is diluted with ethyl acetate (100 ml) and the organic phase is washed in succession with ice-cold 0.5N hydrochloric acid, saturated sodium hydrogen carbonate solution and water, dried over sodium sulfate and concentrated. The pale yellow oily residue is taken up in tetrahydrofuran (160 ml) and, with stirring at –20° C., sodium borohydride (1.12 g) is added in portions thereto. Then over a period of 10 minutes methanol (1.5 ml) is added dropwise thereto (slight exothermic reaction). The temperature of the slightly turbulent mixture is allowed to rise slowly to 0°–5° C. and the mixture is stirred overnight at that temperature, then 1N hydrochloric acid (39 ml) is added dropwise thereto and the aqueous phase is extracted with ethyl acetate (100 ml).

The organic phase is washed neutral with ice-cold 1N sodium carbonate solution (70 ml) and then with saturated sodium chloride solution, dried over magnesium sulfate and concentrated. Drying in a high vacuum yields the title compound in the form of a pale yellow oil (7.18 g, 94%). Analytically pure product (pale yellow oil) is obtained after flash chromatography on silica gel (eluant gradient hexane/ethyl acetate from 5:1 to 3:1): $R_f$ (hexane/-ethyl acetate 1:1)=0.50. $[\alpha]^{25}_D$=+4.6±1.0 (c 1.0, $CH_2Cl_2$). IR ($CH_2Cl_2$) 3620, 2960, 2110, 1770, 1180 $cm^{-1}$. $^1$H-NMR (300 MHz, $CDCl_3$): δ0.92 (d,J=6.9 Hz, 3H), 0.95 (d,J=6.8 Hz, 6H), 1.04 (d,J=6.9 Hz, 3H), 1.35–1.8 (m, 5H), 2.1–2.25 (m, 3H), 2.69 (m, 1H), 3.57 (m, 1H), 3.67 (m, 1H), 3.72 (m, 1H), 4.44 (m, 1H) ppm. $^{13}$C-NMR (75 MHz, $CDCl_3$): δ19.4, 20.2, 21.1, 21.3, 28.0, 30.2, 30.3, 31.1, 43.8, 46.3, 64.9, 65.1, 81.8, 179.4 ppm. $C_{14}H_{25}N_3O_3$(283.4): calc.: C=59.34%, H=8.89%, N=14.83%; found: C=59.35%; H=8.85%; N=14.41%.

EXAMPLE 6: Alternative preparation of 2-{(2(S)-azido-2-[4(S)-isopropyl-5-oxo-tetrahydrofuran- 2(S)-yl]-ethyl}-3(S)-methyl-butanol At 0°–5° C., chloroformic acid ethyl ester (1.38 ml) is added dropwise over a period of 10 minutes to a solution of 4.0 g of 2(S)-[2(S)-azido-2(S)-(4(S)-isopropyl-5-oxo-tetrahydrofuran-2(S)-yl)-ethyl]-3-methyl-butyric acid (crude product from Example 2 or 3) in toluene (80 ml) and the batch is then stirred for 20 minutes at the same temperature. The white suspension is filtered over a glass frit, the precipitate is washed with toluene (30 ml) and the flitrate is concentrated to a volume of 40 ml using a rotary evaporator (bath temperature 35° C.). The clear solution is then diluted with tetrahydrofuran (80 ml) and cooled to 0°–5° C. and, with vigorous stirring, sodium borohydride (0.68 g) and water (1.5 ml) are added in succession thereto. After 3 hours sodium borohydride (0.10 g) is again added and the batch is stirred for a further hour at 0°–5° C. With ice-cooling, 1N hydrochloric acid (30 ml) is added, the aqueous phase is extracted with ethyl acetate (1×100 ml) and the organic phase is washed in succession with 1N sodium carbonate solution (2×20 ml) and saturated sodium chloride solution (3×20 ml). The aqueous phases are each back-extracted with cold ethyl acetate. The combined organic phases are dried over magnesium sulfate and concentrated. Drying in a high vacuum yields the title compound in the form of a pale yellow oil (3.47 g, 92%).

EXAMPLE 7: 2-{2(S)-tert-butoxycarbonylamino-2-[4(S)-isopropyl-5-oxo-tetrahydrofuran,2(S)- yl]-ethyl}-3(S)-methyl-butanol A solution of 24.8 g of 2-{2(S)-azido-2-[4(S)-isopropyl-5-oxo-tetrahydrofuran-2(S)-yl]-ethyl}-3(S)-methyl-butanol (product from Example 5 or 6) in ethyl acetate (250 ml) is hydrogenated in the presence of 10% Pd/C (8.68 g) at room temperature and normal pressure for 24 hours. The reaction mixture is filtered over Hyflo®, washed repeatedly with ethyl acetate and concentrated. The crude 5(S)-[1(S)-amino-3(S)-hydroxymethyl-4-methylpentyl]-3(S)-iso- propyl-dihydrofuran-2-one thus obtained (23.0 g; colourless oil that crystallises out slowly to a wax-like white solid) is dissolved in ethyl acetate (500 ml) and, with stirring at 0°–5° C., first ethyldiisopropylamine (23.7 ml) and then, dropwise, a solution of di-tert-butyl dicarbonate (21.0 g) in ethyl acetate (100 ml) are added to the solution. The reaction mixture is heated to room temperature and then further stirred overnight. The reaction mixture is concentrated and the oily residue is purified by flash chromatography on 250 g of silica gel (2:1 hexane/-ethyl acetate as eluant). The title compound is obtained in the form of a white solid (24.9 g, 80%). M.p. 126°–128° C. (recrystallised from diethyl ether). $^1$H-NMR (300 MHz, CDCl$_3$): δ0.86 (d,J=6.8 Hz, 3H), 0.90 (d,J=6.9 Hz, 3H), 0.94 (d,J=6.8 Hz, 3H), 1.01 (d,J=6.8 Hz, 3H), 1.35–1.7 (m, 3H), 1.44 (s, 9H), 1.74 (m, 1H), 1.96 (m, 1H), 2.05–2.25 (m, 3H), 256 (m 1H), 3.60 (m, 1H), 3.69 (m, 1H), 3.99 (m, 1H), 4.4–4.55 (m, 2H) ppm. $[\alpha]^{25}_D$=/14.9 (c 1.01, CH$_2$Cl$_2$). C$_{19}$H$_{35}$NO$_5$ (357.49): calc.: C=63.84%, H=9.87%, N=3.92%; found: C=63.62% H=9.66%; N=4.05%.

EXAMPLE 8: Dicyclohexylammonium salt of 2(S)-[2(S)-azido-2(S)-(4(S)-isopropyl-5-oxo- tetrahydrofuran-2(S)-yl]-ethyl]-3-methyl-butyric acid Dicyclohexylamine (182 mg) is added at room temperature to a solution of 297 mg of (S)-[2(S)-azido-2(S)-(4(S)-isopropyl-5-oxo-tetrahydrofuran-2(S)-yl)-ethyl]-3-methyl-butyric acid (product from Example 2 or 3) in methanol (5 ml). The mixture is concentrated in a rotary evaporator and the white residue is dried under a high vacuum. The crude salt is then dissolved in ethyl acetate (8 ml) at elevated temperature and clarified by filtration and, with stirring, hexane (8 ml) is added thereto. The reaction mixture is allowed to cool to room temperature and the crystals that have precipitated are filtered off, washed with 3:1 hexane/ethyl acetate and dried under a high vacuum at 50° C. The title compound is obtained in the form of white crystalline solids (360 mg, 75%). M.p. 139°–140° C. $^1$H-NMR (10:1 C$_6$D$_6$/DMSO-d$_6$): δ0.73 (d,J=7Hz, 3H), 0.78 (d,J=7 Hz, 3H), 0.85 (d,J=7 Hz, 3H), 0.92 (d,J=7 Hz, 3H), 0.9–1.2 (m, 11H), 1.43 (m, 2H), 1.5–1.6 (m, 5H), 1.65–1.9 (m, 5H), 1.65–1.69 (m, 7H), 1.94 (m, 1H), 2.36 (m, 1H), 2.4–2.55 (m, 3H), 3.41 (m, 1H), 3.2–4.1 (br s,2H), 4.17 (m, 1H) ppm. C$_{26}$H$_{46}$N$_4$O$_4$0.16 H$_2$O (481.6): calc.: C=64.85%, H=9.70%, N=11.63%; found: C=65.14%; H=9.76%; N=11.47%.

EXAMPLE 9: Further reaction of 2-{2(S)-azido-2-[4(S)-isopropyl-5-oxo-tetrahydrofuran-2(S)-yl]-ethyl}-3(S)-methyl-butyraldehyde to form 5(S)-amino-4(S)-hydroxy-2(S)-isopropyl-7(S)-[4- methoxy-3-(2-methoxymethoxyethyl)-benzyl]-8-methyl-nonanoic acid (N-butyl)amide 1) 5(S)-{{1(S)-azido-3(S)-{(R,S)-hydroxy-[4-methoxy-3-(2-methoxymethoxyethyl) phenyl-methyl}-4-methyl-pentyl}}-3(S)-isopropyl-tetrahydrofuran-2-one A few iodine crystals are added to a suspension of 763 mg of magnesium chips in 0.5 ml of tetrahydrofuran and the suspension is activated in an ultrasound bath for 30 minutes. Then 4 drops of 1,2-dibromoethane and then a solution of 8.64 g of 4-bromo-2-(2-methoxy-methoxyethyl)-anisole in 30 ml of tetrahydrofuran are added dropwise in such a manner that the reaction mixture boils under reflux. When the addition is complete, the reaction mixture is maintained under reflux for a further 1 hour. The reaction mixture is cooled to room temperature and then, with stirring, is added dropwise in the course of 45 minutes to a solution, cooled to −75° C., of 2.85 g of 2-{2(S)-azido-2-[4(S)-isopropyl-5-oxo-tetrahydrofuran-2(S)-yl]-ethyl}-3(S)-methyl-butyraldehyde in 20 ml of tetrahydrofuran. The reaction mixture is stirred further for 150 minutes at −75° C. and then at the same temperature a solution of 1.4 ml of glacial acetic acid in 1 ml of tetrahydrofuran and then 25 ml of saturated ammonium chloride solution are added thereto. The batch is then brought to room temperature, poured onto 60 ml of water and extracted three times with 100 ml of ethyl acetate. The organic phases are washed with 50 ml of saturated sodium chloride solution, combined, dried over magnesium sulfate and concentrated by evaporation. Purification of the residue by means of FC (400 g of silica gel, hexane/ethyl acetate 8:2) yields the title compound: R$_f$ (hexane/ethyl acetate 7:3)=0.25; HPLC R$_t$=48.1 and 50.3 minutes;. (diastereoisomeric mixture).

2) {2(S)-{2(S)-Azido-2-[4(S)-isopropyl-5-oxo-tetrahydrofuran-2(S)-yl]-3-methyl-1(R,S)-[4-methoxy-3-(2-methoxymethoyethyl)-phenyl]-butyl}-isobutyrate 0.25 ml of pyridine, 0.31 ml of isobutyric anhydride and 15 mg of dimethylaminopyridine are added to a solution of 300 mg of 5(S)-{{1(S)-azido-3(S)-{(R,S)-hydroxy-[4-methoxy-3-(2- methoxymethoxyethyl)phenyl-methyl}-4-methyl-pentyl}}-3(S)-isopropyl-tetrahydrofuran-2-one in 3.5 ml of dichloromethane and the reaction mixture is stirred further for 80 hours at room temperature. The reaction mixture is then partitioned between dichloromethane (three times), water (once) and saturated sodium chloride solution (twice). The combined organic phases are dried over magnesium sulfate and concentrated by evaporation and the residue is purified by means of FC (30 g of silica gel, hexane/ethyl acetate 8:2) to yield the title compound: R$_f$ (hexane/ethyl acetate 8:2)=0.26; HPLC R$_t$=21.4 minutes and 21.8 minutes (diastereoisomeric mixture).

3) {(4(S)-Azido-7(S)-butylcarbamoyl-5(S)-hydroxy-2(S)-isopropyl-8-methyl-1(R,S)-[4- methoxy-3-(2-methoxymethoxyethyl)-phenyl]-nonyl)-isobutyrate A solution of 170 mg of {2(S)-{2(S)-azido-2-[4(S)-isopropyl-5-oxo-tetrahydrofuran-2(S)-yl]-ethyl}-3-methyl-1(R,S)-[4-methoxy-3-(2-methoxymethoxyethyl)-phenyl]-butyl}-isobutyrate in 1.4 ml of butylamine is stirred for 16 hours at room temperature and then concentrated by evaporation. Purification of the residue by means of FC (hexane/ethyl acetate 7:3) yields the title compound: R$_f$ (hexane/ethyl acetate 7:3)=0.25; HPLC R$_t$=20.38 and 20.8 minutes (diastereoisomedc mixture).

4) 5(S)-Amino-4(S)-hydroxy-2(S)-isopropyl-7(S)-[4-methoxy-3-(2-methoxymethoxyethyl)- benzyl]-8-methyl-nonanoic acid (N-butyl)amide 50 mg of {4(S)-Azido-7(S)-butylcarbamoyl-5(S)-hydroxy-2(S)-isopropyl-8-methyl-1 (R,S)-[4- methoxy-3-(2-methoxymethoxyethyl)-phenyl]-nonyl}-isobutyrate are hydrogenated in 10 ml of methanol in the presence of 50 mg of 10% Pd/C at room temperature and normal pressure. The reaction mixture is filtered and concentrated by evaporation. The residue is purified by FC (2 g of silica gel, dichloromethane/methanol 9:1). The title compound is obtained: R$_f$ (dichloromethane/methanol 9:1)=0.19; HPLC R$_t$=13.42 minutes; FAB-MS (M+H)$^+$=509.

The 4-bromo-2-(2-methoxymethoxyethyl)-anisole used as starting matedal is prepared as follows:

a) 2-(2-Hydroxyethyl)-anisole 35.3 g of caesium carbonate and then a solution of 6.5 ml of methyl iodide in 40 ml of acetone are added to a solution of 10 g of 2-(2-hydroxyphenyl)-ethanol in 200 ml of acetone. The reaction mixture is stirred for 50 minutes at room temperature, filtered and concentrated by evaporation. The residue is partitioned between diethyl ether and water. The organic phases are combined, dried over magnesium sulfate and concentrated by evaporation and the residue is purified by means of FC (dichloromethane/diethyl ether 97:3) to yield the title compound: $R_f$ (dichloromethane/diethyl ether 97:3)=0.34; HPLC $R_t$=9.31 minutes.

b) 4-Bromo-2-(2-hydroxyethyl)-anisole 35.72 g of tetrabutylammonium tribromide are added in portions to a solution of 10.7 g of 2-(2-hydroxyethyl)-anisole in 195 ml of dichloromethane and 130 ml of methanol. The reaction mixture is stirred for 150 minutes at room temperature and then concentrated by evaporation using a rotary evaporator. The residue is partioned between diethyl ether and water. The organic phases are combined, dried over magnesium sulfate and concentrated by evaporation and the residue is pudfied by means of FC (dichloromethane) to yield the title compound: $R_f$ (dichloromethane)=0.26; HPLC $R_t$=13.0 minutes.

c) 4-Bromo-2-(2-methoxymethoxy-ethyl)-anisole 1.48 g of N-ethyl-diisopropylamine and 0.49 g of chlorodimethyl ether are added at room temperature to a solution of 948 mg of 4-bromo-2-(2-hydroxyethyl)-anisole in 30 ml of dichloromethane. The reaction mixture is stirred further for 200 minutes at room temperature and then 1 ml of water and 1 ml of 25% ammonium hydroxide solution are added thereto. The two-phase mixture is further stirred vigorously for 15 minutes and then the organic phase is separated off, dried over sodium sulfate and concentrated by evaporation. Purification of the residue by means of FC (hexane/dichloromethane 1:1) yields the title compound: $R_f$ (dichloromethane)=0.6; HPLC $R_t$=17.33 minutes.

EXAMPLE 10: Further reaction of 2-{2(S)-azido-2-[4(S)-isopropyl-5-oxo-tetrahydrofuran-2(S)-yl]-ethyl}-3(S)-methyl-butyraldehyde to form 5(S)-amino-4(S)-hydroxy-2(S)-isopropyl-7(S)-[4- 3-hydroxypropoxy)-3-(3-methoxypropoxy)-benzyl]-8-methyl-nonanoic acid N-(2-morpholin-4-yl-ethyl) amide hydrochloride 1) 5(S)-{1(S)-Azido-3(S)-{(R,S)-hydroxy-[4-(3-benzyloxypropoxy)-3-(3-methoxyproxy) -phenyl-methyl}-4-methyl-pentyl}-3(S)-isopropyl-tetrahydrofuran-2-one 1.3 ml of a 0.9M solution of butyllithium in hexane are slowly added dropwise to a solution, stirred at −75° C., of 500 mg of 4-(3-benzyloxypropoxy)-3-(3-methoxypropoxy)-bromobenzene in 2 ml of tetrahydrofuran. The reaction mixture is further stirred for 20 minutes at −75° C. and then a suspension of magnesium bromide freshly prepared at room temperature from 44.5 mg of magnesium powder and 0.158 ml of 1,2-dibromoethane in 3 ml of tetrahydrofuran, is added dropwise thereto. The reaction mixture is stirred further for 30 minutes at −75° C. and then a solution of 172 mg of 2-{2(S)-azido-2-[4(S)-isopropyl-5-oxo- tetrahydrofuran-2(S)-yl]-ethyl}-3(S)-methyl-butyraldehyde in 2 ml of tetrahydrofuran is added dropwise thereto. The reaction mixture is again stirred for 30 minutes at −75° C. and then at the same temperature 1.2 ml of saturated ammonium chloride solution are added dropwise thereto. The reaction mixture is brought to room temperature and extraction is carried out three times with ethyl acetate. The organic phases are washed with water (twice) and saturated sodium chlodde solution (once), dried over magnesium sulfate, combined and concentrated by evaporation and the residue is purified by means of FC (twice 30 g of silica gel, hexane/ethyl acetate 6:2) to yield the title compound: $R_f$ (hexane/ethyl acetate 2: 1)=0.23; HPLC $R_t$=20.3 and 21.1 minutes (diastereoisomeric mixture); FAB-MS M$^+$=611.

2) {2(S)-{2(S)-Azido-2-[4(S)-isopropyl-5-oxo-tetrahydrofuran-2(S)-yl]-3-methyl-1(R,S)-[4-(3-benzyloxypropoxy)-3-(3-methoxypropoxy)-phenyl]-butyl}-acetate A solution of 144 mg of 5(S)-{1(S)-azido-3(S)-{(R,S)-hydroxy-[4-(3-benzyloxypropoxy)-3-(3-methoxypropoxy)-phenyl- methyl}-4-methyl-pentyl}-3(S)-isopropyl-tetrahydrofuran-2-one in 1.8 ml of acetic anhydride and 0.057 ml of pyridine is stirred for 30 hours at room temperature and then concentrated to dryness by evaporation under reduced pressure. The residue is partitioned between dichloromethane (three times) and water/saturated sodium chloride solution (three times). The organic phases are combined, dried over magnesium sulfate and concentrated by evaporation and the residue is purified by means of FC (hexane/ethyl acetate 4:1) to yield the title compound: $R_f$ (hexane/ethyl acetate 2:1)=0.38 and 0.33; HPLC $R_t$=21.8 and 21.8 minutes (diastereoisomeric mixture); FAB-MS M$^+$=653, (M+Na)$^+$=676.

3) 5(S)-{1(S)-Amino-3(S)-[4-(3-hydroxypropoxy)-3-(3-methoxypropoxy)-benzyl]-4-methyl-phenyl}-3(S)-isopropyl-tetrahydrofuran-2-one A solution of 151 mg of {2(S)-{2(S)-azido-2-[4(S)-isopropyl-5-oxo-tetrahydrofuran-2(S)-yl]ethyl}-3-methyl-1 (R,S)-[4-(3-benzyloxypropoxy)-3-(3-methoxypropoxy)-phenyl]-butyl}-acetate in 10 ml of ethanol is hydrogenated for 170 hours in the presence of 70 mg of PdO at normal pressure and room temperature. The reaction mixture is filtered and concentrated by evaporation and the residue is dissolved in 10 ml of ethanol and hydrogenated again for 24 hours in the presence of 140 mg of PdO at normal pressure and room temperature. Fitration and concentration by evaporation yield the title compound in the form of a crude product: $R_f$ (dichloromethane/methanol)=0.32; HPLC $R_t$=11.7 minutes; FAB-MS (M+H)$^+$=480. The compound is used in the next step without being purified.

4) 5(S)-{1(S)-(tert-Butoxycarbonyl)amino-3(S)-[4-(3-hydroxypropoxy)-3-(3-methoxypropoxy)- benzyl]-4-methyl-pentyl}-3(S)-isopropyl-tetrahydrofuran-2-one A solution of 0.07 ml of N-ethyldiisopropylamine in 0.1 ml of dichloromethane and then a solution of 77 mg of di-tert-butyl dicarbonate in 0.4 ml of dichloromethane are added dropwise to a solution, stirred at 0° C., of 106 mg of 5-(S)-{1(S)-amino-3(S)-[4-(3-hydroxypropoxy) -3-(3-methoxypropoxy)-benzyl]-4-methyl-pentyl}-3(S)-isopropyl-tetrahydrofuran-2-one in 4.5 ml of dichloromethane. The reaction mixture is brought to room temperature, stirred further for 20 hours at room temperature and then concentrated to dryness by evaporation. The residue is purified by means of FC (50 g of silica gel, dichloromethane/methanol 98:2) to yield the title compound: $R_f$ (dichloromethane/methanol 95:5)=0.34; HPLC $R_t$=19.1 minutes; FAB-MS M$^+$=579, (M+Na)$^+$=602.

5) 5(S)-(tert-Butoxycarbonyl)amino-4(S)-hydroxy-2(S)-isopropyl-7(S)-[4-(3-hydroxypropoxy)- 3-(3-methoxypropoxy)-benzyl]-8-methyl-nonanoic acid N-(2-morpholin-4-yl-ethyl)amide A mixture of 84 mg of 5(S)-{1(S)-(tert-butoxycarbonyl)amino-3(S)-[4-(3-hydropypropoxy)-3-(3-methoxypropoxy)-benzyl]-4-methyl-pentyl}-3(S)-isopropyl-tetrahydrofuran-2-one, 0.6 ml of 4-(2-aminoethyl)-morpholine and 0.025 ml of glacial acetic acid is stirred for 16 hours at room temperature and 6 hours at 45° C. and then partitioned between diethyl ether (twice) and saturated sodium hydrogen carbonate solution (once) and water (twice). The organic phases are combined, dried over magnesium sulfate and concentrated by evaporation and the residue is purified by means of FC (5 g of silica gel, dichloromethane/methanol 98:2) to yield the title compound: $R_f$ (dichloromethane/ methanol 95:5)=0.16; HPLC $R_t$=14.5 minutes.; FAB-MS $(M+H)^+$=710.

6) 5(S)-Amino-4(S)-hydroxy-2(S)-isopropyl-7(S)-[4-(3-hydroxypropoxy)-3-(3-methoxy-propoxy)-benzyl]-8-methyl-nonanoic acid N-(2-morpholin-4-yl-ethyl)amide hydrochloride 30 mg of 5(S)-(tert-butoxycarbonyl) amino-4(S)-hydroxy-2(S)-isopropyl-7(S)-[4-(3-hydroxypropoxy)-3-(3-methoxypropoxy)-benzyl]-8-methyl-nonanoic acid N-(2-morpholin-4-yl-ethyl)amide are dissolved in 1.5 ml of a 4N solution, cooled to 0° C., of hydrochloric acid in dioxane and the solution is stirred further for 10 minutes at 0° C. The reaction mixture is concentrated to dryness by evaporation under reduced pressure at room temperature. The residue is purified by means of FC (5 g of silica gel, dichloromethane/methanol 98:2) to yield the title compound: $R_f$ (dichloromethane/methanol 8:2)=0.20; $R_t$=10.43 minutes; FAB-MS $(M+H)^+$=610.

The 4-(3-benzyloxypropoxy)-3-(3-methoxypropoxy)-bromobenzene used as starting material is prepared as follows:

a) 2-(3-Methoxypropoxy)-phenol

A solution of 22 g of pyrocatechol in 80 ml of N,N-dimethylformamide is added at room temperature in the course of 30 minutes to a suspension of 8.4 g of sodium hydride (60% dispersion in mineral oil) in 300 ml of dimethylformamide, and the reaction mixture is stirred for 1 hour at room temperature. A solution of 49.3 g of 3-bromopropyl methyl ether in 80 ml of dimethylformamide is then added dropwise thereto. The reaction mixture is stirred further for 80 hours at room temperature and then concentrated by evaporation under reduced pressure at a bath temperature of 30° C. The residue is partitioned between diethyl ether and water. The organic phases are combined, dried over magnesium sulfate and concentrated by evaporation and the residue is purified by means of FC (100 g of silica gel, hexane/dichloromethane 5:95) to yield the title compound: $R_f$ (dichloromethane/diethyl ether 96:4)=0.35; HPLC $R_t$=11.2 minutes.

b) 4-Bromo-2-(3-methoxypropoxy)-phenol 6.9 g of tetrabutylammonium tribromide are added in portions at room temperature to a solution of 2.6 g of 2-(3-methoxypropoxy)-phenol in 60 ml of dichloromethane and 40 ml of methanol. The reaction mixture is concentrated by evaporation and the residue is partitioned between diethyl ether and water. The organic phases are combined, dried over magnesium sulfate and concentrated by evaporation and the residue is purified by means of FC (700 g of silica gel, dichloromethane/diethyl ether 98:2) to yield the title compound: $R_f$ (dichloromethane/diethyl ether 97: 3)=0.50; HPLC $R_t$=14.3 minutes; FAB-MS $(M+H)^+$=262.

c) 4.(3-Benzyloxypropoxy)-3-(3-methoxypropoxy)-bromobenzene

A mixture of 4 g of 4-bromo-2-(3-methoxypropoxy)-phenol, 2.3 g of potassium carbonate, 3.8 g of benzyl-(3-bromopropyl) ether, a spatula tip of sodium iodide and 15 ml of acetonitrile is stirred under reflux for 30 hours. The reaction mixture is filtered and the flitrate is concentrated by evaporation. The residue is partitioned between ethyl acetate and water. The organic phases are combined, dried over magnesium sulfate and concentrated by evaporation and the residue is purified by means of FC (hexane/ethyl acetate 95:5) to yield the title compound: $R_f$ (hexane/ethyl acetate= 9:1)=0.15; HPLC $R_t$=20.7 minutes.

We claim:

1. A compound of formula I

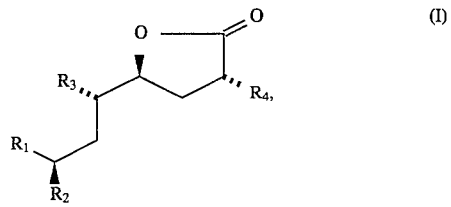

wherein $R_1$ is free or esterified carboxy, hydroxymethyl or formyl, $R_2$ and $R_4$ are each independently of the other aliphatic, cycloaliphatic-aliphatic, araliphatic or heteroarylaliphatic radicals, and $R_3$ is azido, or amino that is aliphatically or araliphatically substituted and/or protected by an amino-protecting group, or a salt thereof.

2. A compound according to claim 1 of formula I wherein $R_1$ is carboxy, lower alkoxycarbonyl, unsubstituted or lower alkyl-, lower alkoxy-, halo-and/or trifluoromethyl-substituted phenyl-lower alkoxycarbonyl, hydroxymethyl or formyl, $R_2$ and $R_4$ are each independently of the other lower alkyl radicals, lower alkenyl, lower alkoxy or lower alkylthio, 3- to 7-membered cycloalkyl-lower alkyl radicals, unsubstituted or lower alkyl-, lower alkoxy-, hydroxy-, halo-, nitro- and/or amino-substituted phenyl-lower alkyl or naphthyl-lower alkyl radicals or unsubstituted or lower alkyl-, lower alkoxy-, hydroxy-, halo-, nitro- and/or amino-substituted pyridyl-lower alkyl, indolyl-lower alkyl, quinolinyl-lower alkyl, pyrimidinyl-lower alkyl, furyl-lower alkyl, benzofuranyl-lower alkyl or thienyl-lower alkyl, and $R_3$ is azido, lower alkylamino, di-lower alkylamino, lower alkanoylamino or N-lower alkanoyl-N-lower alkyl-amino, unsubstituted or lower alkyl-, lower alkoxy-, hydroxy-, halo-, nitro-and/or amino-substituted phenyl-lower alkylamino, N-lower alkyl-N-phenyl-lower alkyl-amino or N-lower alkanoyl-N-phenyl-lower alkyl-amino or N-lower alkoxycarbonylamino, N-lower alkyl-N-lower alkoxycarbonyl-amino, N-lower alkanoyl-N-lower alkoxycarbonyl-amino, N-lower alkoxycarbonyl-N-phenyl-lower alkylamino, N-phenyl-lower alkoxycarbonylamino, N-lower alkyl-N-phenyl-lower alkoxycarbonyl-amino, N-lower alkanoyl-N-phenyl-lower alkoxycarbonyl-amino, N-phenyl-lower alkoxycarbonyl-N-phenyl-lower alkylamino, N-tri-lower alkylsilylamino, N-lower alkyl-N-tri-lower alkylsilyl-amino, N-lower alkanoyl-N-tri-lower alkylsilyl-amino or N-tri-lower alkylsilyl-N-phenyl-lower alkylamino, or a salt thereof.

3. A compound according to claim 1 of formula I wherein $R_1$ is carboxy, $R_2$ is $C_1$–$C_4$ alkyl, $R_4$ is $C_1$–$C_4$alkyl, $C_2$–$C_4$alkenyl, or phenyl-$C_1$–$C_4$alkyl that is unsubstituted or substituted by $C_1$–$C_4$alkyl, by $C_1$–$C_4$alkoxy, by hydroxy, by halogen having an atomic number of up to and including 35, by nitro and/or by amino, and $R_3$ is azido, $C_1$–$C_4$alkoxycarbonylamino or phenyl-$C_1$–$C_4$alkoxycarbonylamino, or a salt thereof.

4. A compound according to claim 1 being 2(S)-[2(S)-Azido-2(S)-(4(S)-isopropyl-5-oxo-tetrahydrofuran-2(S)-yl)-ethyl]-3-methyl-butyric acid or a salt thereof.

5. A compound according to claim 1 being 2-{2(S)-Azido-2-[4(S)-isopropyl-5-oxo-tetrahydrofuran-2(S)-yl]-ethyl}-3(S)-methyl-butyraldehyde or a salt thereof.

6. A compound according to claim 1 being 2-{2(S)-Azido-2-[4(S)-isopropyl-5-oxo-tetrahydrofuran-2(S)-yl]-ethyl}-3(S)-methyl-butanol or a salt thereof.

7. A compound according to claim 1 being 3(S)-Isopropyl-5(S)-(1(S)-(tert-butoxycarbonyl)amino)-3(S)-isopropyl-4-hydroxy-butyl)-tetrahydrofuran-2-one or a salt thereof.

* * * * *